United States Patent [19]
Liu et al.

[11] Patent Number: 5,770,431
[45] Date of Patent: Jun. 23, 1998

[54] *BACILLUS THURINGIENSIS* STRAINS ACTIVE AGAINST LEPIDOPTERAN AND COLEOPTERAN PESTS

[75] Inventors: Chi-Li Liu; Lee Fremont Adams; Patricia A. Lufburrow; Michael David Thomas, all of Davis, Calif.

[73] Assignee: Abbott Laboratories, Abbott Park, Ill.

[21] Appl. No.: 433,783

[22] Filed: May 3, 1995

Related U.S. Application Data

[60] Division of Ser. No. 337,358, Nov. 10, 1994, which is a continuation-in-part of Ser. No. 264,100, Jun. 22, 1994, abandoned, which is a continuation-in-part of Ser. No. 194,651, Feb. 9, 1994, abandoned, which is a continuation-in-part of Ser. No. 166,391, Dec. 13, 1993, abandoned, which is a continuation-in-part of Ser. No. 991,073, Dec. 15, 1992, abandoned.

[51] Int. Cl.$^6$ ............................ C12N 15/32; C12N 15/63; C12N 1/21
[52] U.S. Cl. ........................... 435/252.3; 536/23.71; 435/69.1; 435/71.3; 435/172.3; 435/252.33; 435/370.1
[58] Field of Search .................. 536/23.71; 435/69.1, 435/71.3, 172.3, 252.3, 252.33, 320.1

[56] References Cited

U.S. PATENT DOCUMENTS

| | | | |
|---|---|---|---|
| 4,910,016 | 3/1990 | Gaertner et al. | 424/93 |
| 5,024,837 | 6/1991 | Donavan et al. | 424/93 |

FOREIGN PATENT DOCUMENTS

93/04587  3/1993  WIPO.

*Primary Examiner*—Rebecca E. Prouty
*Attorney, Agent, or Firm*—Michael J. Ward

[57] ABSTRACT

The invention is related to a novel biologically pure *Bacillus thuringiensis* (*B.t.*) strains active against lepidopteran and coleopteran pests which produces a bipyramidal crystal consisting essentially of at least two delta-endotoxins having a molecular weight of about 130,000 daltons and a rhomboidal crystal consisting essentially of two delta-endotoxins, each having a molecular weight of about 33,000 daltons, as well as spores, crystals, delta-endotoxins and/or mutants thereof. The invention also relates to insecticidal compositions obtainable therefrom. The invention further relates to methods of using the insecticidal compositions to control an insect pest(s) from the order Lepidoptera and/or Coleoptera. The invention also relates to isolated DNA sequences encoding the delta-endotoxins.

28 Claims, 4 Drawing Sheets

```
              10         20         30         40         50         60
    MIVDLYRYLGGLAAVNAVLHFYEPRPDICRNISEEYNLI---VFGDRIPTFSIDPSQININNLSVDTPVDEI
                          ||         |                        |  |  |
                MAIMN---DIAQDAARAWDIIAGPFIRPGTTPTNRQLFNYQIGNIEVE--PGNL
                  X          10        20         30         40
    70        80        90        100       110       120       130
    TINNVRSIQLISS--RFENTGFVDTENYFTPELSRTVVNSISTSTTTGYKYTQSLTVSSKFSFNFPVAGAEN
       |       |   |  ||           | | |       ||  | | |        | ||    |   |
    NFSVVPELDFSVSQDLFNNTSVQQSQT-ASFNESRT--ETTSTAVTHGVKSGVTVSASAKFNAKILVKSIEQ
    50        60        70        80        90        100       110

140       150       160       170       180       190       200
    NISFSVGFEQNLSTTETKTESTSTLMRIPPQPVSVRP--RTAKRVEISLFELAIPRIQNEISGFV---TGTL
      |  |  | | | | |         |  |||  | |        |         |    |  |   ||||
    TITTTVSTEYNFSSTTTRTNTVTRGWSI-AQPVLVPPHSRVTATLQIYKGDFTVPVL---LSLRVYGQTGTL
    120       130       140       150       160       170       180

210       220       230       240       250       260       270
    PTISNSHISDLYAVLTRTDSL--CPNSYINRDDFLRIDHENRGLGLQGF--GSLTGNLTSLDFAIRTTEYDL
      |  |||  |    |       |       |         |     ||   | |
    -AGNPSFPS-LYA-ATYENTLLGRIREHIAPPALFRASNAYISNGVQAIWRGTATTRVSQGLYSVVRIDERP
       190       200       210       220       230       240       250

280       290    X
    PSNTIINIENEIKRAHILTQ
                 |
    LAGYSGETRT-YYLPVTLSNSSQILTPGSLGSEIPIINPV
       260       270    X    280       290
```

FIG.3A

```
                  X          10         20         30         40         50
                  MIVDL--YRYLGGLAAVNAVLHFYEPRPDICRNISEEYNLIVFGDRIPTFSI
                       ||     |         |          |           ||
WVRYNQFRRELTLTVLDIVALFSNYDSRRYP--IRTVSQLTREIYTNPVL-ENF--DGSFRGMAQRIEQNIR
  230         240       X 250       260        270        280        290

60         70         80         90        100        110
DPSQINI-NNLSVDTPV----DEITINNVRSIQLISS--RFENTGFVDTENYFTPEL-SRTVVNSISTSTTT
 |    ||    ||              |   |   |   |   |    | | ||          |
QPHLMDILNSITIYTDVHRGFNYWSGHQITASPVGFSGPEFAFPLFGNAGNAAPPVLVSLTGLGIFRTLSSP
       300        310        320        330        340        350        360

120        130        140        150        160        170        180
GYKYTQSLTVSSKFSFN--FPVAGAENNISFSVGFEQNLSTTETKTESTSTLMRIPPQPVSVRPRTAKRVFI
|    |         |   |     ||          ||            |    ||||  || ||
LYR---RIILGSGPNNQELFVLDGTE--FSFASLTTNLPSTIYRQRGTVDSLDVIPPQDNSVPPRAG----F
     370        380        390        400        410        420

190        200        210        220        230        240        250
SLFELAIPRIQNEISGFV-TGTLPTISNSHIS-DLYAVLTRTDSLCPNSYINR-DDFLRIDHENRGLGLQGF
|  |         |||    ||  |  |                                     |  |
S-HRLSHVTMLSQAAGAVYTLRAPTFSWQHRSAEFNNIIPSSQ--ITQIPLTKSTNLGSGTSVVKGPGFTGG
     430        440        450        460        470        480        490

260        270        280        290    X
GSL----TGNLTSLDFAIRTTEYD-----LPSNTIINIENEIKRAHILTQ
 |       |    |           |
DILRRTSPGQISTLRVNITAPLSQRYRVRIRYASTTNLQFHTSIDGRDINQGNFSATMSSGSNLQSGSFR
  500        510        520        530        540      X 550        560
```

FIG.3B 5,770,431

BACILLUS THURINGIENSIS STRAINS ACTIVE AGAINST LEPIDOPTERAN AND COLEOPTERAN PESTS

This application is a divisional application of application Ser. No. 08/337,358, filed Nov. 10, 1994, which is a continuation-in-part of application Ser. No. 08/264,100, filed Jun. 22, 1994, now abandoned, which is a continuation-in-part of Ser. No. 08/194,651, filed Feb. 9, 1994, now abandoned, which is a continuation-in-part of application Ser. No. 08/166,391, filed Dec. 13, 1993, now abandoned which is a continuation-in-part of application Ser. No. 07/991,073, filed Dec. 15, 1992, now abandoned.

1. FIELD OF THE INVENTION

The invention is related to a novel biologically pure *Bacillus thuringiensis* (*B.t.*) strain(s) active against lepidopteran and coleopteran pests which produces a bipyramidal crystal consisting essentially of at least two delta-endotoxins having a molecular weight of about 130,000 daltons and a rhomboidal crystal consisting essentially of two delta-endotoxins, each having a molecular weight of about 33,000 daltons, as well as spores, crystals, delta-endotoxins and/or mutants thereof. The invention also relates to insecticidal compositions obtainable therefrom. The invention further relates to methods of using the insecticidal compositions to control an insect pest(s) from the order Lepidoptera and/or Coleoptera. The invention also relates to isolated DNA sequences encoding the delta-endotoxins.

2. BACKGROUND OF THE INVENTION

Every year, significant portions of the world's commercially important agricultural crops, including foods, textiles, and various domestic plants are lost to pest infestation, resulting in losses in the millions of dollars. Various strategies have been used in attempting to control such pests.

One strategy is the use of broad spectrum pesticides, chemical pesticides with a broad range of activity. However, there are a number of disadvantages to using such chemical pesticides. Specifically, because of their broad spectrum of activity, these pesticides may destroy non-target organisms such as beneficial insects and parasites of destructive pests. Additionally, these chemical pesticides are frequently toxic to animals and humans, and targeted pests frequently develop resistance when repeatedly exposed to such substances.

Another strategy has involved the use of biopesticides, which make use of naturally occurring pathogens to control insect, fungal and weed infestations of crops. Biopesticides are naturally occuring organisms that produce a toxin(s), a substance toxic to the infesting agent which is generally less harmful to non-target organisms and the environment as a whole than chemical pesticides.

The most widely used biopesticide is *Bacillus thuringiensis* (*B.t.*). *B.t.* is a widely distributed, rod shaped, aerobic and spore forming microorganism. During its sporulation cycle, *B.t.* produces a protein(s) known as a delta-endotoxin (s), that forms crystalline inclusion bodies within the cell. The delta-endotoxins have molecular weights ranging from 27–140 kD and kill insect larvae upon ingestion.

Delta-endotoxins have been produced by recombinant DNA methods (see, for example, Tailor et al., 1992, Molecular Microbiology 6:1211–1217; toxin is active against lepidopteran and coleopteran pests; Payne et al., U.S. Pat. No. 5,045,469; toxin is active against lepidopteran pests). The delta-endotoxins produced by recombinant DNA methods may or may not be in crystal form.

A number of *B.t.* strains have been isolated that have been found to be active against insect pests of the order Lepidoptera. *B.t.* subsp. *kurstaki* HD-1 produces bipyramidal and cuboidal crystal proteins in each cell during sporulation (L üthy et al., in Microbial and Viral Pesticides, ed. E. Kurstak, Marcel Dekker, New York, 1982, pp. 35–74); the bipyramidal crystal was found to be encoded by three cryIA genes (Aronson et al., 1986, Microbiol. Rev. 50:1–50). *B.t.* subsp. *kurstaki* HD-73 crystal delta-endotoxin contains the CryIA (c) protein (Adang et al., 1985, Gene 36:289–300). *B.t.* subsp. *dendrolimus* HD-7 and HD-37 contain a CryIA and a CryII protein; *B.t.* subsp. *sotto* contains an alkaline soluble protein that differs from the holotype CryIA(a) protein by 24 amino acids; *B.t.* subsp. *subtoxicus* HD-10 contains CryIA and CryIB proteins; *B.t.* subsp. *tolworthi* HD-121 contains CryIA and CryII proteins; and *B.t.* subsp. *aizawai* HD-68 contains CryIA proteins (Hofte and Whiteley, 1989, Microbiol. Reviews 53:242–255). Payne, U.S. Pat. No. 4,990,332, issued Feb. 5, 1993, discloses an isolate of *B.t.*, PS85AI, and a mutant of the isolate, PS85AI, which both have activity against *Plutella xylostella*, a lepidopteran pest, and produce alkaline soluble proteins having a molecular weight of 130,000 and 60,000 daltons. Payne, U.S. Pat. No. 5,045,469, issued Sep. 3, 1991 discloses a *B.t.* isolate designated PS81F which also produces alkaline soluble proteins having a molecular weight of 130,000 and 60,000 daltons and has activity against *Spodoptera exigua* and *T. ni;* the toxin gene from PS81F appears to have little homology to the toxin gene from *B.t.* subsp. *kurstaki* HD-1. Payne, U.S. Pat. No. 5,206,166, filed Jun. 25, 1992, issued Apr. 27, 1993, discloses *B.t.* isolates PS81A2 and PS81RR1 which produce 133,601 and 133,367 dalton alkaline-soluble proteins; both have activity against *Trichoplusia ni, Spodoptera exigua* and *Plutella xylostella* and are different from *B.t.* subsp. *kurstaki* HD-1 and other *B.t.* isolates. Bernier et al., U.S. Pat. No. 5,061,489 and WO 90/08434 discloses strain A20 producing a delta-endotoxin encoded by at least three genes: 6.6-, 5.3-, and 4.5-type genes (cryIA(a), cryIA(b), and cryIA(c)). Chestukhina et al., 1988, FEBS Lett. 232:249–51, disclose that *B.t.* subsp. *galleriae* produces two delta-endotoxins, both of which are active against lepidopteran pests.

Other strains, e.g. *Bacillus thuringiensis* subsp. *tenebrionis* (Krieg et al., 1988, U.S. Pat. No. 4,766,203), have been found to be specific for Coleoptera. The isolation of another coleopteran toxic *Bacillus thuringiensis* strain was reported in 1986 (Hernnstadt et al. Bio/Technology vol. 4, 305–308, 1986, U.S. Pat. No. 4,764,372, 1988). This strain, designated "*Bacillus thuringiensis* subsp. *san diego*", M-7, has been deposited at the Northern Regional Research Laboratory, U.S.A. under accession number NRRL B-15939. However, the assignee of the '372 patent, Mycogen, Corp. has publicly acknowledged that *Bacillus thuringiensis* subsp. *san diego* is *Bacillus thuringiensis* subsp. *tenebrionis*.

Other isolated strains have been found to be active against two orders of pests. Padua, 1990, Microbiol. Lett. 66:257–262, discloses the isolation of two mutants containing two delta-endotoxins, a 144 kD protein having activity against a lepidopteran pest and a 66 kD protein having activity against mosquitoes. Bradfish et al., U.S. Pat. No. 5,208,017, discloses *B.t.* isolates PS86A1 and PS86Q3 which produce alkaline soluble proteins having a molecular weight of 58,000 and 45,000 daltons and 155,000, 135,000, 98,000, 62,000, and 58,000 daltons, respectively and which have activity against lepidopteran and coleopteran pests. PCT Application No. WO 90/13651 and Tailor et al., 1992, Molecular Microbiology 6:1211–1217, disclose a *B.t.* strain which is toxic against Lepidoptera and Coleoptera and which produces a toxin having a molecular weight of 81 kd.

It is advantageous to isolate new strains of *Bacillus thuringiensis* to produce new toxins so that there exists a wider spectrum of biopesticides for any given insect pest.

3. SUMMARY OF THE INVENTION

The invention is related to a novel biologically pure *Bacillus thuringiensis* strain(s) or a spore(s), crystal(s) or mutant(s) thereof which strain or mutant in contrast to *B.t.* strains disclosed in the prior art, has activity against an insect pest of the order Lepidoptera and an insect pest of the order Coleoptera, produces at least two delta-endotoxins having a molecular weight of about 130,000 daltons and two delta-endotoxins both having molecular weights of about 33,000 daltons. One of the 33,000 dalton delta-endotoxins has an amino acid sequence essentially as depicted in SEQ ID NO:37 (hereinafter referred to as the "MIVDL protein"). The other 33,000 dalton delta-endotoxin has an amino acid sequence essentially as depicted in SEQ ID NO:38 (hereinafter referred to as the "MKHHK protein"). The 130,000 delta-endotoxins have insecticidal activity against insect pests of the order Lepidoptera.

The invention also relates to each of the delta-endotoxins as well as an isolated nucleic acid fragment containing a nucleic acid sequence encoding each of the delta-endotoxins or a portion of the delta-endotoxin having insecticidal activity against a pest. In one embodiment, the nucleic acid fragment contains a nucleic acid sequence encoding the MIVDL protein and may have the nucleic acid sequence essentially as depicted in SEQ ID NO:39. In another embodiment, the nucleic acid fragment contains a nucleic acid sequence encoding the MKHHK protein and may have the nucleic acid sequence essentially as depicted in SEQ ID NO:40. The invention is also directed to a genomic sequence comprising nucleic acid sequence encoding the MKHHK and/or MIVDL and Lay have the nucleic acid sequence essentially as depicted in SEQ ID NOS:41 (MKHHK and MIVDL), 44 (MKHHK), and 45 (MIVDL).

The invention also provides vectors, DNA constructs and recombinant host cells comprising the claimed nucleic acid fragment(s), which vectors, DNA constructs and recombinant host cells are useful in the recombinant production of the delta-endotoxins of the present invention. The nucleic acid fragment may be operably linked to transcription and translation signals capable of directing expression of the delta-endotoxin in the host cell of choice. Recombinant production of the delta-endotoxin(s) of the invention is achieved by culturing a host cell transformed or transfected with the nucleic acid fragment of the invention, or progeny thereof, under conditions suitable for expression of the delta-endotoxin, and recovering the delta-endotoxin from the culture.

The invention is further related to an oligonucleotide probe having a nucleotide sequence essentially as depicted in SEQ ID NO:20 which can be used to detected the MIVDL protein and and oligonucleotide probe essentially as depicted in SEQ ID NO:21 which can be used to detect the MKHHK protein.

In a specific embodiment of the invention, the thuringiensis strain of the present invention is EMCC0075 and EMCC0076 having the identifying characteristics of NRRL B-21019 and NRRL B-21020 respectively.

The novel *Bacillus thuringiensis* strains, spores, mutants or crystals and/or delta-endotoxins may within the scope of this invention each be formulated into insecticidal compositions. In one embodiment, the strain, spores, mutants, crystals, and/or delta-endotoxins may be combined with an insecticidal carrier. Insecticidal compositions comprising the strains or mutants of the invention and/or spores, and/or crystals thereof may be used to control insect pests of the order Lepidoptera and and/or insect pests of the order Coleoptera in a method comprising exposing the pest to an insect-controlling effective amount of such an insectidical composition.

Furthermore, the compositions or delta-endotoxins of the present invention may be used to enhance the insecticidal activity of another *Bacillus*-related insecticide. As defined herein, "a *Bacillus* related insecticide" is a *Bacillus* (e.g., *Bacillus thuringiensis*, specifically, *Bacillus thuringiensis* subsp. *kurstaki* or *Bacillus thuringiensis* subsp. *tenebrionis* or *Bacillus subtilis*) strain, spore, or substance, e.g., protein or fragment thereof having activity against or which kill insects; a substance that provides plant protection, e.g. antifeeding substance; or a microorganism capable of expressing a *Bacillus* gene encoding a *Bacillus* protein or fragment thereof having activity against or which kills insects (e.g., *Bacillus thuringiensis* delta-endotoxin) and an acceptable carrier (see Section 5.2., infra, for examples of such carriers). A microorganism capable of expressing a *Bacillus* gene encoding a *Bacillus* protein or fragment thereof having activity against or which kill insects inhabits the phylloplane (the surface of the plant leaves), and/or the rhizosphere (the soil surrounding plant roots), and/or aquatic environments, and is capable of successfully competing in the particular environment (crop and other insect habitats) with the wild-type microorganisms and provide for the stable maintenance and expression of a *Bacillus* gene encoding a *Bacillus* protein or fragment thereof having activity against or which kill insects. Examples of such microorganisms include but are not limited to bacteria, e.g., genera *Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, Alcaligenes,* and *Clostridium;* algae, e.g. families *Cyanophyceae, Prochlorophyceae, Rhodophyceae, Dinophyceae, Chrysophyceae, Prymnesiophyceae, Xanthophyceae, Raphidophyceae, Bacillariophyceae, Eustigmatophyceae, Cryptophyceae, Euglenophyceae, Prasinophyceae,* and *Chlorophyceae;* and fungi, particularly yeast, e.g., genera *Saccharonmyces, Cryptococcus, Kluyveromyces, Sporobolomyces, Rhodotorula,* and *Aureobasidium.*

In a specific embodiment, the delta-endotoxins or compositions of the present invention may act together with Bacillus-related insecticides in a synergistic fashion. In another embodiment, *Bacillus* strains active against insect pests of the order Coleoptera may act together in a synergistic fashion with delta-endotoxins, *Bacillus* strains or spores thereof active against insect pests of the order Lepidoptera to kill insect pests of the order Coleoptera. In yet another embodiment, the delta-endotoxins of the present invention may act together in a synergistic fashion.

4. BRIEF DESCRIPTION OF THE FIGURES

FIG. 1 shows the results of PCR analysis of *Bacillus thuringiensis* strains for cryI genes by agarose gel electrophoresis. Lane 1 shows molecular weight markers (1 kb ladder, BRL-GIBCO). Lanes 2 and 3 show analysis of strains EMCC0075 and EMCC0076 with cryID oligonucleotide primers described in FIG. 1. Lanes 4–6 show the analysis of *Bacillus thuringiensis* subsp. *tenebrionis*, an unknown *Bacillus thuringiensis* strain, and *Bacillus thuringiensis* subsp. *aizawai* with cryID oligonucleotide primers. *Bacillus thuringiensis* subsp. *tenebrionis* contains only the cryIIIA gene; the unknown *Bacillus thuringiensis* strain does not contain the cryID gene; and *Bacillus thuringiensis* subsp. *aizawai* contains several cryI genes including cryID.

FIGS. 3A and 3B shows the homology of the "MIVDL" protein to the 34 kDa protein of *Bacillus thuringiensis* subsp. *thompsoni* and the CryIA(a) protein of *Bacillus thuringiensis* subsp. *kurstaki*.

5. DETAILED DESCRIPTION OF THE INVENTION

5.1. Obtaining Delta-Endotoxins

Figure 1:
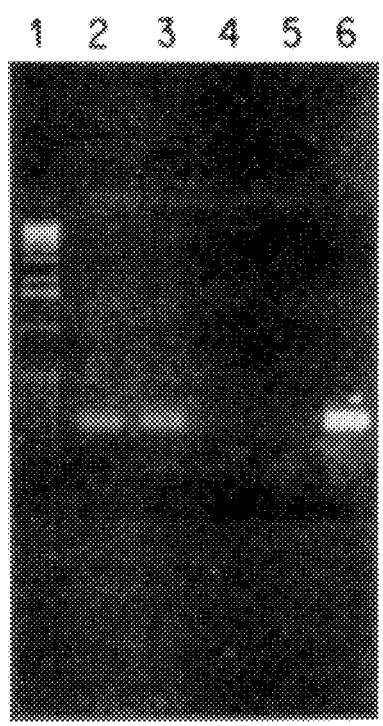

The spores and crystals of the present invention are obtainable from the strains of the present invention. The strains of the present invention may be cultured using media and fermentation techniques known in the art (see, for example, Rogoff et al., 1969, J. Invertebrate Path. 14:122–129; Dulmage et al., 1971, J. Invertebrate Path. 18:353–358; Dulmage et al., in Microbial Control of Pests and Plant Diseases, H. D. Burges, ed., Academic Press, N.Y., 1980). Upon completion of the fermentation cycle, the crystals and spores can be harvested by separating *B.t.* spores and crystals from the fermentation broth by means well known in the art, e.g. centrifugation. The spores and crystals are contained in the pellet.

As noted in Section 2, supra, crystals consist essentially of a delta-endotoxin(s). The strains of the present invention produce two types of crystals. One is a bipyramidal crystal consisting essentially of at least two 130,000 dalton delta-endotoxins. The other is a rhomboidal crystal consisting essentially of the two 33,000 dalton delta-endotoxins.

Purification of the crystals or delta-endotoxins can be carried out by various procedures known in the art, including, but not limited to, density gradient centrifugation, chromatography (e.g. ion exchange, affinity, hydrophobic and size exclusion), electrophoretic procedures, differential solubility, or any other standard technique for the purification of proteins.

The delta-endotoxins may also be obtained from a recombinant DNA expression system. Specifically, DNA encoding each toxin as, for example, essentially depicted in SEQ ID NOS:39, 40, 44, and 45 is cloned into a suitable DNA expression vector. Alternatively one genomic DNA fragment comprising nucleic acid sequences encoding each delta endotoxin as, for example, essentially depicted in SEQ ID NO:41 may be cloned.

Identification of the specific DNA fragment encoding the delta-endotoxin may be accomplished in a number of ways, including, but not limited to, electrophoretic separation of the fragments (Southern, 1975, J. Mol. Biol. 98:503) in agarose, transfer of the separated DNA fragments to nitrocellulose, nylon, or other suitable support medium, and probing of the transferred fragments with a degenerate oligonucleotide probe(s) based on the amino acid sequence of the protein as determined by sequential Edman degradation. Alternatively, one may probe with a labeled gene fragment corresponding to the open reading frame of a protein with suspected high homology to the protein of interest. High homology to the gene of interest may be determined by alignment of a family of related proteins and identification of highly conserved regions in the encoding DNA segments (see, for example, Gribskov, K., and J. Devereux, eds., in Sequence Analysis Primer, Stockton Press, N.Y., 1991). An elegant and reliable method is to determine the amino acid sequences of at least two peptide fragments, generated by enzymatic or chemical means from the protein of interest, design degenerate oligonucleotides that will recognize the DNA encoding those regions, and then to apply polymerase chain reaction (PCR) techniques to amplify perfect or near-perfect copies of the intervening region of DNA. This PCR-generated segment of DNA can then be labeled and used as a highly specific probe for cloning the delta-endotoxin-encoding gene.

Once identified, the DNA fragment harboring the gene encoding the delta-endotoxin or a portion thereof may be cloned by ligation of a size-selected library of fragments expected to harbor the gene of interest into a suitable vector, including, but not limited to, pBR322, pUC118, pACYC194 and PBCSK plasmids and their variants for transformation into *Escherichia coli;* or pUB110, pBD64, pBC16, pHP13, pE194, pC194, and their variants, for transformation into *Bacillus* spp. Bacteriophage vectors, such as lambda and its derivatives, may also be used for cloning of the gene(s) into *E. coli.*

Production of the delta-endotoxin or a portion thereof at commercially useful levels can be achieved by subcloning the encoding gene into plasmid vectors that permit stable expression and maintenance in a suitable host. Frequently, acceptable expression can be achieved using the native regulatory elements present on the DNA fragment encoding the delta-endotoxin. However, one might wish to add or alter transcriptional regulatory signals (promoters, initiation start sites, operators, activator regions, terminators) and translational regulatory signals (ribosomal binding sites, initiation codons) for enhanced or more regulated expression of the delta-endotoxin gene within the chosen host cell.

In addition to plasmids, delta-endotoxin genes and the appropriate regulatory elements may be introduced into one of the native plasmids of *Bacillus thuringiensis* and/or other chosen host, or into the chromosomal DNA, via "gene conversion" (e.g., Iglesias and Trautner, 1983, Mol Gen. Genet. 189:73–76; Duncan et al., 1978, Proc. Natl. Acad. Sci. U.S.A. 75:3664–3665) or homologous recombination (e.g., Ferrari et al., 1983, J. Bacteriol. 154:1513–1515) at sites of shared DNA homology between the vector and the host strain. An efficient "two-plasmid" system may be used for introduction of genes into Bacilli via homologous recombination (see, for example, PCT Patent WP91/09129). Transposons may also be used to introduce cry genes into the selected host strain. For example, in the Bacilli, transposons such as Tn917 and its derivatives may be used (Youngman et al., 1989, In Regulation of Prokaryotic DeveLopmeiit, I. Smith, R. Slepecky, and P. Setlow, eds. American Society for Microbiology, Washington, D.C.).

Transfer of cloned delta-endotoxin genes into *Bacillus thuringiensis,* as well as into other organisms, may be achieved by a variety of techniques, including, but not limited to, protoplasting of cells (Chang and Cohen, 1979, Mol. Gen. Genet. 168: 111–115; Crawford et al., 1987, J. Bacteriol. 169: 5423–5428); electroporation (e.g., Schurter et al., 1989, Mol. Gen. Genet. 218: 177–181 and Macaluso et al., 1991, J. Bacteriol. 173: 1353–1356); particle bombardment (e.g., Shark et al., 1991, Appl. Environ. Microbiol. 57:480–485); silicon carbide fiber-mediated transformation of cells (Kaeppler et al., 1992, Theor. Appl. Genet. 84:560–566); conjugation (Gonzalez et al., 1982, Proc. Natl. Acad. Sci. U.S.A. 79:6951–6955); or transduction by bacteriophage (e.g., Lecadet et al., 1992, Appl. Environ. Microbial. 58: 840–849). Transformed colonies may be detected by their ability to produce crystal delta-endotoxin, to bind antibody directed against that specific delta-endotoxin, or to kill susceptible pests, e.g., arthropods or nematodes, in bioassay.

Criteria for selection of a particular host for production include, but are not limited to, ease of introducing the gene into the host, availability of expression systems, and stable maintenance and expression of the gene encoding the delta-endotoxin. The host may be a microorganism, such as *Bacillus thuringiensis* itself, or an inhabitant of the phytosphere, e.g., the phylloplane (the surface of plants), and/or the rhizosphere (the soil surrounding plant roots), and/or aquatic environments, and should be capable of competing in the particular environment (crop and other insect habitats) with the wild-type microorganisms. Examples of such microorganisms include but are not limited to bacteria, e.g. genera *Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, Alcaligenes,* and *Clostridium;* algae, e.g. families *Cyanophyceae, Prochlorophyceae, Rhodophyceae, Dinophyceae, Chrysophyceae, Prymnesiophyceae, Xanthophyceae, Raphidophyceae, Bacillariophyceae, Eustigmatophyceae, Cryptophyceae, Euglenophyceae, Prasinophyceae,* and *Chlorophyceae;* and fungi, particularly yeast, e.g. genera *Saccharomyces, Cryptococcus, Kluyveromyces, Sporobolomyces, Rhodotorula,* and *Aureobasidium.*

The gene(s) encoding the delta-endotoxin(s) of the present invention or a portion thereof can also be inserted into an appropriate cloning vector for subsequent introduction into the genomes of suitable plants that are known to be infested with insects susceptible to the delta-endotoxin(s), or into specific baculoviruses which can in turn be directly used as insecticides.

Figure 2:
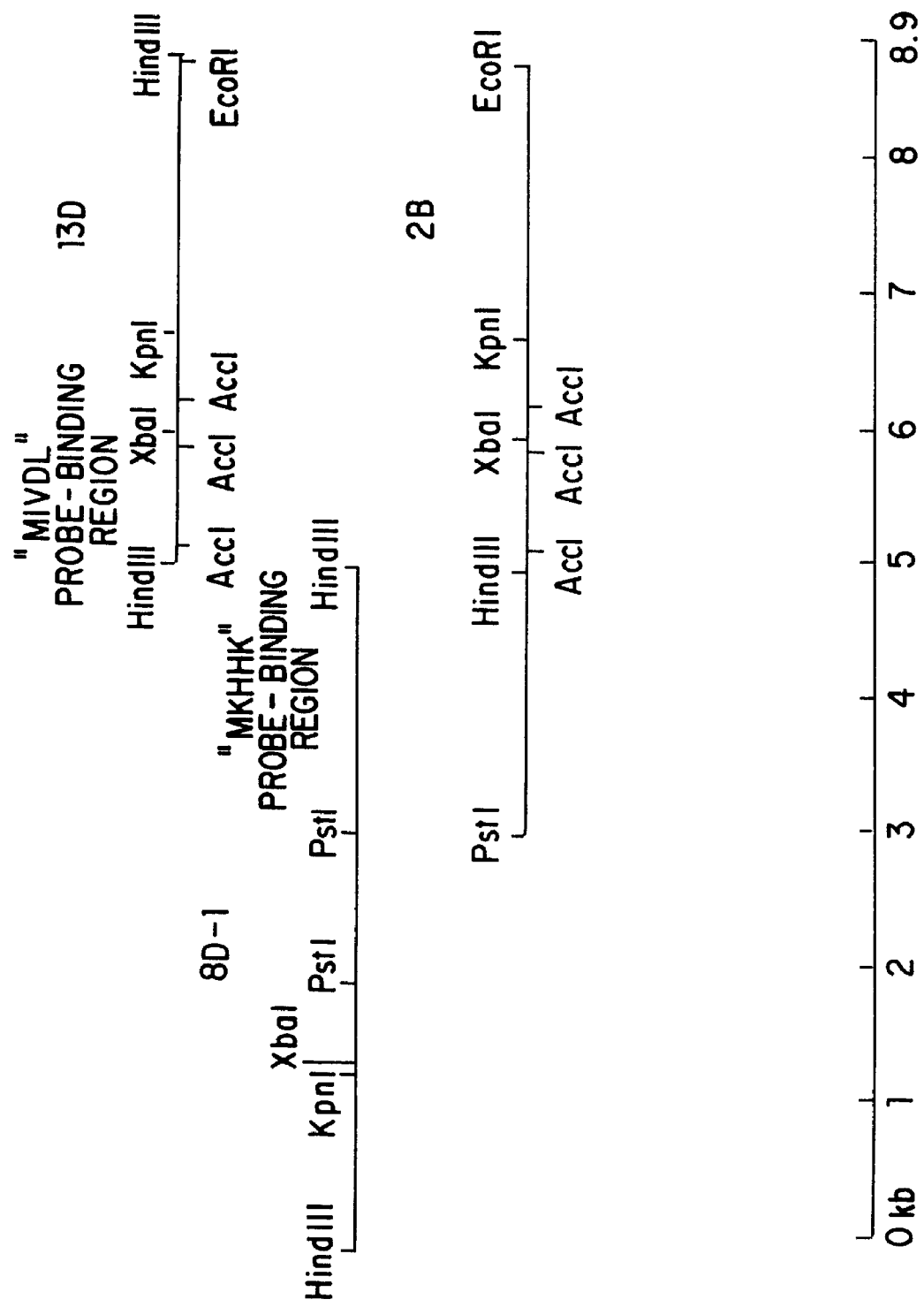
FIG. 2 shows the cloned DNA fragments which encode the MKHHK and MIVDL proteins.

Those skilled in the art will recognize that the invention is not limited to use of the nucleic acid fragments specifically disclosed herein, for example, in SEQ ID NO:39 OR 40. It will be apparent that the invention also encompasses those nucleotide sequences that encode the same amino acid sequences as depicted in SEQ ID NO:39 OR 40, but which differ from those specifically depicted nucleotide sequences by virtue of the degeneracy of the genetic code. The invention specifically encompasses any variant nucleotide sequence, and the protein encoded thereby, which protein retains at least about an 80%, preferably 90%, and most preferably 95% homology or identity with one or the other of the amino acid sequences depicted in FIG. 2 and retains the activity of the sequences described herein. In particular, variants which retain a high level (i.e., >80%) of homology at highly conserved regions of said delta-endotoxin are contemplated. Furthermore, the invention encompasses any variant that hybridizes to the nucleotide sequence of the delta-endotoxin under the following conditions presoaking in 5× SSC and prehybridizing for 1 hr. at about 40° C. in a solution of 20% formamide, 5× Denhardt's solution, 50 mM sodium phosphate, pH 6.8, and 50 ug denatured sonicated calf thymus DNA, followed by hybridization in the same solution supplemented with 100 uM ATP for 18 hrs. at about 40° C., followed by a wash in 0.4× SSC at a temperature of about 45° C.

Useful variants within the categories defined above include, for example, ones in which conservative amino acid substitutions have been made, which substitutions do not significantly affect the activity of the protein. By conservative substitution is meant that amino acids of the same class may be substituted by any other of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln. It will be apparent to the skilled artisan that such substitutions can be made outside the regions critical to the function of the molecule and still result in an active delta-endotoxin. Retention of the desired activity can readily be determined by using the assay procedures described below.

5.2. Mutants

The invention is also directed to a mutant *B.t.* strain which produces a larger amount of and/or larger crystals than the parental strain. A "parental strain" as defined herein is the original *Bacillus thuringiensis* strain before mutagenesis.

To obtain such mutants, the parental strain may, for example, be treated with a mutagen by chemical means such as N-methyl-N'-nitro-N-nitrosoguanidine or ethyl methanesulfonate, or by irradiation with gamma rays, X-rays or UV. Specifically, in one method of mutating *Bacillus thuringiensis* strains and selecting such mutants the following procedure is used:

i) the parental strain is treated with a mutagen;

ii) the thus presumptive mutants are grown in a medium suitable for the selection of a mutant strain; and iii) the mutant strain is selected for increased production of delta-endotoxin.

According to a preferred embodiment of this method, the selected colonies are grown in a production medium, and a final selection for strains capable of increased delta-endotoxin production is performed.

Alternatively, the mutant(s) may be obtained using recombinant DNA methods known in the art. For example, a DNA sequence containing a gene coding for a delta-endotoxin may be inserted into an appropriate expression vector and subsequently introduced into the parental strain using procedures known in the art. Alternatively, a DNA sequence containing a gene coding for a delta-endotoxin may be inserted into an appropriate vector for recombination into the genome and subsequent amplification.

5.3. Bioassay

The activity of the *B.t.* strains of the present invention or spores, mutants, crystals, or delta-endotoxins thereof against various insect pests may be assayed using procedures known in the art, such as an artificial insect diet incorporation assay, artificial diet overlay, leaf painting, leaf dip, and foliar spray. Specific examples of such assays are given in Section 6, infra.

5.4 Compositions

The strains, spores, crystals, delta-endotoxins, or mutants of the present invention described supra can be formulated with an acceptable carrier into an insecticidal composition(s) that is, for example, a suspension, a solution, an emulsion, a dusting powder, a dispersible granule, a wettable powder, an emulsifiable concentrate, an aerosol or impregnated granule.

Such compositions disclosed above may be obtained by the addition of a surface active agent, an inert carrier, a preservative, a humectant, a feeding stimulant, an attractant, an encapsulating agent, a binder, an emulsifier, a dye, a U.V.

protectant, a buffer, a flow agent, or other component to facilitate product handling and application for particular target pests.

Suitable surface-active agents include but are not limited to anionic compounds such as a carboxylate, for example, a metal carboxylate of a long chain fatty acid; an N-acylsarcosinate; mono or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine as an acetate, naphthenate or oleate; an oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates or botanical materials such as wood products, cork, powdered corncobs, peanut hulls, rice hulls, and walnut shells.

The compositions of the present invention can be in a suitable form for direct application or as a concentrate or primary powder which requires dilution with a suitable quantity of water or other diluent before application. The insecticidal concentration will vary depending upon the nature of the particular formulation, specifically, whether it is a concentrate or to be used directly. The composition contains 1 to 98% of a solid or liquid inert carrier, and 0 to 50%, preferably 0.1 to 50% of a surfactant. These compositions will be administered at the labeled rate for the commercial product, preferably about 0.01 lb–5.0 lb per acre when in dry form and at about 0.01 pts–10 pts per acre when in liquid form.

In a further embodiment, the strains, spores, crystals, delta-endotoxins or mutants of the present invention can be treated prior to formulation to prolong the pesticidal activity when applied to the environment of a target pest as long as the pretreatment is not deleterious to the crystal delta-endotoxin. Such treatment can be by chemical and/or physical means as long as the treatment does not deleteriously affects the properties of the composition(s). Examples of chemical reagents include, but are not limited to, halogenating agents; aldehydes such as formaldehyde and glutaraldehyde; anti-infectives, such as zephiran chloride; alcohols, such as isopropranol and ethanol; and histological fixatives, such as Bouin's fixative and Helly's fixative (see, for example, Humason, Animal Tissue Techniques, W.H. Freeman and Co., 1967).

The compositions of the invention can be applied directly to the plant by, for example, spraying or dusting at the time when the pest has begun to appear on the plant or before the appearance of pests as a protective measure. Plants to be protected within the scope of the present invention include, but are not limited to, cereals (wheat, barley, rye, oats, rice, sorghum and related crops), beets (sugar beet and fodder beet), drupes, pomes and soft fruit (apples, pears, plums, peaches, almonds, cherries, strawberries, raspberries, and blackberries), leguminous plants (alfalfa, beans, lentils, peas, soybeans), oil plants (rape, mustard, poppy, olives, sunflowers, coconuts, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages and other brassicae, carrots, onions, tomatoes, potatoes, paprika), lauraceae (avocados, cinnamon, camphor), deciduous trees and conifers (e.g. linden-trees, yew-trees, oak-trees, alders, poplars, birch-trees, firs, larches, pines), or plants such as maize, turf plants, tobacco, nuts, coffee, sugar cane, tea, vines, hops, bananas and natural rubber plants, as well as ornamentals. In most cases, the preferred mode of application is by foliar spraying. The preferred mode of application for soil pests is by furrow application or by "lay-by" application. It is generally important to obtain good control of pests in the early stages of plant growth as this is the time when the plant can be most severely damaged. The spray or dust can conveniently contain another pesticide if this is thought necessary. In a preferred embodiment, the compositions of the invention is applied directly to the plant.

The compositions of the present invention may be effective against pests including, but not limited to, pests of the order Lepidoptera, e.g. *Achroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis, Archips* sp., *Argyrotaenia* sp., *Athetis mindara, Bombyx mori, Bucculatrix thurberiella, Cadra cautella, Choristoneura* sp., *Cochylis hospes, Colias eurytheme, Corcyra cephalonica, Cydia latiferreanus, Cydia pomonella, Datana integerrima, Dendrolimus sibericus, Desmia funeralis, Diaphania hyalinata, Diaphania nitidalis, Diatraea grandiosella, Diatraea saccharalis, Ennomos subsignaria, Boreuma loftini, Ephestia elutella, Erannis tiliaria, Estigmene acrea, Eulia salubricola, Eupoecilia ambiguella, Euproctis chrysorrhoea, Euxoa messoria, Galleria mellonella, Grapholita molesta, Harrisina americana, Helicoverpa subflexa, Helicoverpa zea, Heliothis virescens, Hemileuca oliviae, Homoeosoma electellum, Hyphantria cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrsisalis, Malacosoma* sp., *Mamestra brassicae, Mamestra configurata, Manduca quinquemaculata, Manduca sexta, Maruca testulalis, Melanchra picta, Operophtera brumata, Orgyia* sp., *Ostrinia nubilalis, Paleacrita vernata, Papilio cresphontes, Pectinophora gossypiella, Phryganidia californica, Phyllonorycter blancardella, Pieris napi, Pieris rapae, Plathypena scabra, Platynota flouendana, Platynota sultana, Platyptilia carduidaetyla, Plodia interpunctella, Plutella xylostella, Pontia protodice, Pseudaletia unipuncta, Pseudoplusia includens, Sabulodes aegrotata, Schizura concinna, Sitotroga cerealella, Spilonota ocellana, Spodoptera* sp., *Thaurnstopoea pityocampa, Tineola bisselliella, Trichoplu-* sia ni, Udea rubigalis, Xylomyges curialis, Yponomeuta padella; Coleoptera, e.g., Leptinotarsa sp., Acanthoscelides obtectus, Callosobruchus chinensis, Epilachna varivestis, Pyrrhalta luteola, Cylas formicarius elegantulus, Listronotus oregonensis, Sitophilus sp., Cyclocephala borealis, Cyclocephala immaculate, Macrodactylus subspinosus, Popillia japonica, Rhizotrogus majalis, Alphitobius diaperinus, Palorus atzeburgi, Tenebrio molitor, Tenebrio obscurus, Tribolium castaneum, Tribolium confusum, Tribolius destructor.

In specific embodiments, a composition comprising the 130,000 dalton delta-endotoxins and/or the two 33,000 dalton delta-endotoxins is effective against lepidopteran pests. Compositions comprising the strains of the present invention are also effective against lepidopteran and coleopteran pests.

The following examples are presented by way of illustration, not by way of limitation.

6. EXAMPLES

6.1. Example 1: Cultivating B.t. Strains EMCC0075 AND EMCC0076

Subcultures of EMCC0075 and EMCC0076, maintained on Nutrient Broth Agar slants, are used to inoculate 250 ml baffled shake flasks containing 50 ml of medium with the following composition:

| | |
|---|---|
| Corn Steep liquor | 15 g/l |
| Maltrin-100 | 40 g/l |
| Potato Starch | 30 g/l |
| $KH_2PO_4$ | 1.77 g/l |
| $K_2HPO_4$ | 4.63 g/l |

The pH of the medium is adjusted to 7.0 using 10N NaOH.

After inoculation, shake flasks are incubated at 30° C. on a rotary shaker with 250 rpm shaking for 72 hours. The *B.t.* crystals and spores, obtained in the above fermentation, are recovered by centrifugation at 15,000 rpm for 15 minutes using a Sorvall RC-5B centrifuge.

6.2. Example 2: Testing of *B.t.* Strains EMCC0075 AND EMCC0076 Spores and Crystals EMCC0075 and EMCC0076 are cultivated in shake flasks as described in Example 1, supra. To determine if EMCC0075 and EMCC0076 are active against lepidopteran pests, a 1:50 dilution of culture broth is made. 5 ml of such diluted culture broth is transferred into a 50 ml polypropylene centrifuge tube. 20 ml of artificial insect diet containing antibiotics is added into the centrifuge tube. The mixture is subsequently dispensed into bioassay trays. Three to six eggs either of beet armyworm (*Spodoptera exigua*) or tobacco budworm (*Heliothis virescens*) are applied on the surface of the "diet". Mylar is ironed onto the bioassay trays and the trays are incubated at 28° C. Scoring is carried out at 7 and 11 days.

To determine if EMCC0075 and EMCC0076 are active against insect pests of the order Coleoptera, 5 ml of the culture broths are removed from the shake flasks and transferred directly into the 50 ml polypropylene centrifuge tubes. 20 ml of artificial insect diet (containing known antibiotics) are then added into the tubes (final testing concentration=20% w/w) and mixed vigorously. The mixtures are then dispensed into bioassay trays. Three to six eggs of corn rootworm (*Diabrotica undecimpunctata*) are applied to the surface of the "diet". Mylar is ironed onto the bioassay trays and the trays are incubated at 28° C. Scoring is carried out at 7 and 11 days.

The bioactivity of EMCC0075 and EMCC0076 towards *Spodoptera exigua* and *Diabrotica undecimpunctata* is expressed in terms of stunt score (SS). The stunt score is determined after incubating the trays for 7 days. In this system, 4=full size larvae (control larvae); 3=¾ size of control larvae; 2=½ size of control larvae; 1=¼ size of control larvae; and 0=mortality. The smaller the number, the higher the *B.t.* activity. The results are shown in Table I. It is evident that EMCC0075 and EMCC0076 possess activity against both lepidopteran and coleopteran pests.

TABLE I

| | *Spodoptera exigua* | *Diabrotica undecimpunctata* | *Heliothis virescens* |
|---|---|---|---|
| EMCC0075 | 1.7 | 0.9 | 1.5 |
| EMCC0076 | 1.8 | 1.8 | 1.8 |
| Control | 4.0 | 4.0 | 4.0 |

6.3. Example 3: cry Gene Profile for EMCC0075 AND EMCC0076

The cry gene profile for EMCC0075 and EMCC0076 is determined by using the PCR method which is described in the Perkin Elmer Cetus Gene Amp® PCR Reagent Kit literature. Double-stranded DNA is heat-denatured and the two oligonucleotides corresponding to the cryIA(a) gene (listed in the Sequence Listing as SEQ ID NO:3 and SEQ ID NO:4 respectively), cryIA(b) gene (listed in the Sequence Listing as SEQ ID NO:5 and SEQ ID NO:6 respectively), cryIA(c) gene (listed in the Sequence Listing as SEQ ID NO:7 and SEQ ID NO:8 respectively), cryID gene (listed in the Sequence Listing as SEQ ID NO:9 and SEQ ID NO:10 respectively), cryIIIA gene (listed in the Sequence Listing as SEQ ID NO:11 and SEQ ID NO:12 respectively), cryIIIB gene (listed in the Sequence Listing as SEQ ID NO:13 and SEQ ID NO:14 respectively), cryIIIC gene (listed in the Sequence Listing as SEQ ID NO:15 and SEQ ID NO:16 respectively), and cryIIID gene (listed in the Sequence Listing as SEQ ID NO:17 and SEQ ID NO:18 respectively), are annealed at temperature and then extended at an intermediate temperature.

PCR analysis indicated that both strains contain a cryID-like gene. A probe specific to cryID also detected a cryID-like gene in Southern analysis of restricted genomic DNA from both strains. No PCR amplifications are observed with primers to cryIA(a), cryIA(b), cryIA(C), cryIB (SEQ ID NOS:22 and 23), cryIC (SEQ ID NOS:24 and 25), cryID, cryIE (SEQ ID NOS:26 and 27), cryIF (SEQ ID NOS:28 and 29), or cryIG (SEQ ID NOS:30 and 31), nor to cryIIA (SEQ ID NOS:32 and 33), cryIIB (SEQ ID NOS:34 and 33), or cryIIC (SEQ ID NOS: 35 and 36), nor to cryIIIA, cryIIIB, cryIIIC, or cryIIID. However, Southern analysis of a restriction fragment from genomic DNA from EMCC0075 and EMCC0076 with a probe that can detect cryIA(a), cryIA(b), and cryIA(c) confirmed the presence of a cryIA-like gene.

6.4. Example 4: Purification of EMCC0075 Bipyramidal and Rhomboidal Crystals A subculture of EMCC0075, maintained on a Nutrient Broth agar plate, is used to inoculate a 2.0 liter baffled shake flask containing 500 ml of medium with the same composition as described in Example 5, infra.

After inoculation, the shake flask is incubated at 30° C. on a rotary shaker for 72 hours at 250 rpm. The crystals and spores are recovered by centrifugation at 10,000 rpm (Sorvall GSA rotor) for 30 minutes. The pellets are washed with deionized water, centrifuged at 15,000 rpm (Sorvall SS34 rotor), and resuspended in deionized water by sonication to a concentration of 0.1 g wet weight per 25 ml. 1 g wet weight crude crystals are diluted to 33.2 ml with deionized water and placed in a 250 ml separatory funnel. The bottom phase solution comprised of 10 ml 3M sodium chloride, 23.4 ml 20% polyethylene glycol 8000, and 33.4 ml 20% sodium dextran sulfate is added to the 250 ml separatory funnel and mixed, followed by 100 ml of a polyethylene glycol upper phase solution comprised of 0.3 g sodium dextran sulfate, 70.3 g polyethylene glycol 8000, and 17.5 g sodium-chloride per liter deionized water. The suspension is shaken vigorously, and the two phases are allowed to separate at room temperature for 30 minutes.

The upper phase which contains large quantities of spores is removed with a pipet. The lower phase contains crystals and residual spores. The extraction is repeated several times until the upper phase contains essentially no spores. The lower phase is then diluted with 100 ml deionized water, and centrifuged at 10,000 rpm (Sorvall GSA rotor) for 45 minutes at 5° C. to recover the crystals. The recovered crystals are washed with 200 ml deionized water, and recentrifuged as before. The spores from the upper phase are also recovered using the above washing procedure.

The bipyramidal and rhomboidal crystals are then further purified by density gradient centrifugation using a discontinuous Ludox™ HS-40 (DuPont) gradient comprised of 3.8 ml each of 75%, 50%, and 38% Ludox™ v/v adjusted to pH 2.5 with 0.2M Tris-HCl. 10 mg of crystals in 100 µl deionized water are layered on the top of the gradient, and centrifuged in a Beckman Ultracentrifuge at 10,000 rpm (Beckman 41 Ti rotor) for 15 minutes at 20° C. Four separate bands are obtained. One contains pure rhomboidal crystals and another contains pure bipyramidal crystals. The two other bands contains mixtures of the two crystal types. The pure crystal bands are recovered, washed with deionized water, and used for bioassay.

6.5. Example 5: SDS-PAGE Analysis of the Delta-Endotoxins from EMCC0075 and EMCC0076

Subcultures of EMCC0075 and EMCC0076, maintained on Nutrient Broth agar plates, are used to inoculate 250 ml baffled shake flasks containing 50 ml of medium with the following composition:

| | |
|---|---:|
| Glucose | 2.0 g/l |
| KH$_2$PO$_4$ | 0.86 g/l |
| K$_2$HPO$_4$ | 0.55 g/l |
| Sodium Citrate | 2.0 g/l |
| CaCl$_2$ | 0.1 g/l |
| MnCl$_2$.4H$_2$O | 0.16 g/l |
| MgCl$_2$.6H$_2$O | 0.43 g/l |
| ZnCl$_2$ | 0.007 g/l |
| FeCl$_3$ | 0.003 g/l |
| Casamino Acids | 5 g/l |

After inoculation, the shake flasks are incubated at 30° C. on a rotary shaker for 72 hours at 250 rpm. The *B.t.* crystals obtained in the above fermentations of EMCC0075 and EMCC0076 are recovered by centrifugation at 10,000 rpm (Sorvall GSA rotor) for 30 minutes. The *B.t.* crystals are then purified by biphasic extraction using sodium dextran sulfate and polyethylene glycol as outlined in Example 4, supra.

*B.t.* crystal preparations from EMCC0075 and EMCC0076 are analyzed by SDS-PAGE. Specifically, the SDS-PAGE is carried out on 10–15% gradient gels using Pharmacials Phast System. The protein bands are analyzed on a Pharmacia densitometer using Pharmacia Gelscan™ Software. The results indicated that the crystals produced by both strains contain at least two proteins with molecular weights of approximately 130,000 daltons and 33,000 daltons.

6.6. Example 6: Bioassay using *Spodoptera exigua* to Determine Activity of Novel Lepidopteran Active *Bacillus thuringiensis* Strains To determine if purified bipyramidal and rhomboidal crystals are active against lepidopteran pests, the crystals are bioassayed against *Spodoptera exigua* using a surface overlay assay. Samples of crystal preparations are applied to individual wells of a jelly tray containing 500 µl of solidified artificial insect diet per well. The trays containing the various samples are air dried. Two to four 2nd or early 3rd instar *Spodoptera exigua* are added to each well containing the dried test sample. The trays are then sealed with Mylar punched with holes for air exchange and are incubated for 3 days at 30° C. The degree of stunting, as described in Example 2, supra, is then recorded.

The results are shown in Table II. It is evident that, surprisingly, both the bipyramidal crystal and the rhomboidal crystal possess activity against *Spodoptera exigua*. The spores also show activity against *Spodoptera exigua*.

TABLE II

| Sample | Wet Weight | Stunt score |
|---|---|---|
| No crystals or spores | — | 4 |
| Rhomboidal & bipyramidal | 2.5 mg/well | 1 |
| crystals and spores | 5.0 mg/well | 0–1 |
| Both crystals, no spores | 2.5 mg/well | 1 |
|  | 10 mg/well | 0–1 |
| Bipyramidal crystals | 0.092 mg/well | 1 |
|  | 0.48 mg/well | 0–1 |
| Rhomboidal crystals | 0.05 mg/well | 1 |
|  | 0.1 mg/well | 0–1 |
|  | 0.5 mg/well | 0 |
| Spores | 10 mg/well | 0–1 |
|  | 20 mg/well | 0 |

6.7. Example 7: Bioassay Against *Diabrotica undecimpunctata*

The coleopteran activity of the whole culture broth of EMCC0075, prepared as described in EXAMPLE 1, is bioassayed against *Diabrotica undecimpunctata* using a micro-diet incorporation bioassay. Specifically, artificial diet is prepared comprised of water, agar, sugar, casein, wheat germ, methyl paraben, sorbic acid, linseed oil, cellulose, salts, propionic acid, phosphoric acid, streptomycin, chlortetracycline, and vitamins. The artificial diet is developed to allow samples consisting of rehydrated dry powders and liquids to be incorporated at a rate of 20% v/v. The test sample is prepared in microcentrifuge tubes to yield eight serial dilutions. The whole broth sample is tested neat at 200 µl/ml, and then diluted in 0.1% Tween 20 to contain 132 µl/ml, 87 µl/ml, 66 µl/ml, 44 µl/ml, 30 µl/ml, 20 µl/ml, and 13 µl/ml. The molten mixture is vortexed and pipetted in 0.1 ml aliquots into 10 wells of a 96 well microtiter plate. Control samples containing 0.1% Tween 20 are dsipensed into 16 wells. Once the diet has cooled and solidified, two neonate *Diabrotica undecimpunctata* larvae are added to each well, and the trays are covered with a perforated sheet of clear mylar. The trays are then incubated for five days at 28°±20° C. and 65% relative humidity.

After five days, insect mortality is rated. The mylar sheet is removed and each well of the microtiter plate is inspected using a dissecting microscope. Larvae that do not move when prodded with a dissecting needle are counted as dead. Percent mortality is calculated, and the data is analyzed via parallel probit analysis. The $LC_{50}$, $LC_{90}$, slope of regression lines, coefficient of variation (CV), and potencies are determined.

The results as shown in Table III indicate the whole culture broth from EMCC-0075 has a $LC_{50}$ and a $LC_{90}$ of 51 μl/ml diet and 170 μl/ml diet, respectively, against *Diabrotica undecimpunctata*.

TABLE III

| $LC_{50}$ μl/ml | $LC_{90}$ μl/ml | Slope | CV | N |
|---|---|---|---|---|
| 51 | 170 | 2 | 7 | 8 |

6.8. Example 8: Protein Sequencing of the Delta-Endotoxins from the Rhomboidal Crystal Proteins of EMCC0075

60 μl of 50% trifluoroacetic acid (TFA) are added to 25 μg of rhomboidal crystals. Four 15 μl aliquots of the mixture are spot dried onto a Biobrene-coated and TFA-pretreated microcartridge glass fiber filter. N-terminal sequencing is performed on a Applied Biosystems Inc. Protein Sequencer Model 476A with on-line HPLC and liquid phase TFA delivery. HPLC determination of phenylthiohydantoin-amino acids is achieved by using the Premix buffer system (ABI Inc.). Data is collected on a Macintosh IIsi using ABI's 610 data analysis software.

A double sequence is observed at approximately a 60/40 ratio. Data are analyzed and the sequences are sorted as follows:

"MIVDL": MIVDLYRYLGGLAAVNAVLHFYEPRP (SEQ ID NO:1)

"MKHHK": MKHHKNFDHI (SEQ ID NO:2)

6.9. Example 9: Cloning of the Genes Encoding the "MIVDL" and "MKHHK" Proteins"

The amino acid sequence initially determined for the "MIVDL" protein, MIVDLYRYLGGLAAVNAVLHFYEPRP, is encoded by the sequence ATG ATH GTN GAY YTN TAY MGN TAY YTN GGN GGN YTN GCN GCN GTN AAY GCN GTN YTN CAY TTY TAY GAR CCN MGN CCN (SEQ ID NO:19). Based on this sequence, a 71 nt oligomer is designed, where mixed deoxynucleotides are used at the 2-fold redundant positions and deoxyinosine at the 4-fold redundant positions to decrease both base discrimination at mismatches and selectivity at incorrect bases (Martin, F. H., and M. M. Castro, 1985, Nucleic Acids Res. 13: 892–8938): ATG ATI GTI GAY YTI TAY MGI TAY YTI GGI GGI YTI GCI GCI GTI AAY GCI GTI YTI CAY TTY TAY GAR CC (SEQ ID NO:20).

The amino acid sequence determined for the "MKHHK" protein, namely, MKHHKNFDHI, permitted design of a more discriminating probe because of the absence of amino acids specified by more than two codons. Further discrimination is permitted by the assumption that As or Ts would be used in the coding sequence in preference to Gs or Cs, due to the overall low % G+C content of *B.t.* strains (approx 34 moles %, Claus, D., and R. C. W. Berkeley. 1986. Genus *Bacillus,* p. 1112. In P. H. A. Sneath (ed.), Bergey's manual of systematic bacteriology, v. 2. The Williams and Wilkins Co., Baltimore). The following probe is synthesized: ATG AAA CAT AAA AAT TTT GAT CAT AT (SEQ ID NO:21). Both the MIVDL and the MKHHK probes are tailed with digoxygenin-dUTP according to the manufacturer's instructions (Boerhinger-Mannheim Genius System™ Users Guide, Version 2.0).

EMCC0075 genomic DNA is digested with EcoRI, EcoRV, HindIII, PstI, or combinations of those enzymes overnight in buffers supplied by the manufacturers, electrophoresed through 0.8% agarose in 0.5× TBE (TRIS-borate-EDTA buffer; Sambrook et al., 1989, in Molecular Cloning, a Laboratory Manual, Cold Spring Laboratory Press, Cold Spring Harbor, N.Y.), transferred in 10× SSC to Boehringer Mannheim nylon membrane with a Stratagene Posiblotter in 10× SSC, and then probed as described below. The MIVDL probe, after hybridization and stringent washing at 48° C. with 0.5× SSC, detected EcoRV and PstI fragments 12 kb or more in size, an ECoRI fragment of approx 10 kb, and a HindIII fragment of approx 3.5 kb. The MKHHK probe, after hybridization and stringent washing at 48° C. with 5× SSC, detected the same size EcoRI, EcoRV, and PstI fragments as did the MIVDL probe. This result indicates that the two genes lie in close proximity to each other. Additionally, the MKHHK probe detected a HindIII fragment of approx 6 kb.

To clone the HindIII fragments encoding at least part of the "MIVDL" and "MKHHK" proteins, pUC118 is digested with HindIII, and then treated with calf intestinal phosphatase to dephosphorylate the 5' ends and thus prevent vector religation. Restricted and phosphatased pUC118 is then mixed with FMCC0075 genomic DNA that had been previously digested to completion with HindIII. After ligation, the reaction mix is used to transform *E. coli* strain XL1-Blue MRF' (Stratagene, Inc., La Jolla, Calif.). Colonies harboring the desired DNA fragment are detected by "colony hybridization" with the aforementioned "MIVDL" and "MKHHK" probes by the procedure described by Sambrook et al., 1989, Molecular cloning, A Laboratory Manual, Cold Spring Laboratory Press, Cold Spring Harbor, N.Y. Three fragments are cloned with the "MIVDL" and "MKHHK" probes (see FIG. 2). *E. coli* containing the "13D" MIVDL gene fragment aew referred to as EMCC0117 cells; *E. coli* containing the "8D-1" MKHHK gene fragment are referred to as EMCC0118 cells; *E. coli* containing the "2B" fragment of the MIVDL and MKHHK genes are referred to as EMCC0118 cells.

6.10. Example 10: Sequencing of the Genes Encoding the "MIDVDL" and "MKHHK" Proteins Nested deletions of three cloned fragments described in EXAMPLE 9 are performed according to the method of Henikoff (Gene 28:351–359, 1984) with a Promega "Erase-a-Basel" kit. Nested deletion sets encompassing the region of interest are sequenced by the dideoxy method (Sanger et al., 1977, PNAS U.S.A. 74:5463–5467) with an ABI 373A sequencer. Sequence correction is performed with SeqEd v 1.0.3; sequence is assembled with MacVector 4.1.1 and AssemblyLIGN v 1.0.7; and additional alignments and searches are performed with the IntelliGenetics Suite Programs, v 5.4.

The determined nucleotide (nt) sequence encoding the MKHHK and MIVDL proteins are shown in SEQ ID NO:39 and 40. The deduced amino acid sequence of the MKHHK and MIVDL proteins is shown underneath their corresponding DNA sequence. The amino acid sequence determined by N-terminal Edman degradation as described in EXAMPLE 8 is in complete agreement with the sequences deduced from the nucleotide sequence. The genomic DNA sequence is shown in SEQ ID NOS:41 (MKHHK and MIVDL), 44 (MKHHK), and 45 (MIVDL).

The MKHHK and MIVDL genes encode proteins with calculated molecular masses of 32,719 and 32,866 daltons. The MKHHK protein aligns poorly with any deduced protein from the EMBL, GeneSeq, or GenBank sequence databases. The MIVDL protein has weak regional homology with the 34 kdal gene of *B. thuringiensis* subsp. *thompsoni* as shown in FIG. 3 (SEQ ID NO:42) (Brown and Whiteley, 1990, J. Bacteriology 174:549–557). In addition, the MIVDL protein has weak regional homologies with CryIA (a) (SEQ ID NO:43) (see FIG. 3). These weak homologies do not correspond to the any of the 5 conserved blocks of Cry toxins described by Hofte and Whiteley (Microbiol. Rev. 53:242–255, 1989).

A nucleotide analysis of the region encoding the MKHHK and MIVDL genes shows ribosome binding sites (AAGGAGT and AAGGTGG, respectively) that differ by one nucleotide with the canonical ribosome binding site of *B. subtilis* (AAGGAGG, which is presumably similar to the *B. thuringiensis* RBS). There is a reasonable transcriptional terminator downstream of the MIVDL gene.

7. DEPOSIT OF MICROORGANISMS

The following strains of *Bacillus thuringiensis* have been deposited in the Agricultural Research Service Patent Culture Collection Laboratory (NRRL), Northern Regional Research Center, 1815 University Street, Peoria, Ill., 61604, U.S.A.

| Strain | Accession Number | Deposit Date |
| --- | --- | --- |
| EMCC0075 | NRRL B-21019 | December 3, 1992 |
| EMCC0076 | NRRL B-21020 | December 3, 1992 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122 and under conditions of the Budapest Treaty. The deposit represents a biologically pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope invention in addition to those shown and described herein will become apparent to those skilled in the art from the foregoing description. Such modifications are also intended to fall within the scope of the appended claims.

Various references are cited herein, the disclosures of which are incorporated by reference in their entireties.

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Met  Ile  Val  Asp  Leu  Tyr  Arg  Tyr  Leu  Gly  Gly  Leu  Ala  Ala  Val  Asn
  1              5                         10                        15

Ala  Val  Leu  His  Phe  Tyr  Glu  Pro  Arg  Pro
                20                    25
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide (x i) SEQUENCE DESCRIPTION: SEQ ID NO:2:

```
Met  Lys  His  His  Lys  Asn  Phe  Asp  His  Ile
 1              5                        10
```

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:3:

CTGCTCCAGC TGCTTGGCTC  20

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:4:

GAATTATACT TGGTTCAGGC CC  22

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:5:

GCACACCTTA CATTTTAAAG CA  22

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:6:

AGATTACAAG CGGATACCAA CATCGCG  27

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:7:

TGGCACTTTC AAAATAACCA A  21

( 2 ) INFORMATION FOR SEQ ID NO:8:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

GCATCGGATA GTATTACTCA AATCCC 26

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

CGCTCTAACA TAGACCTTAT AA 22

( 2 ) INFORMATION FOR SEQ ID NO:10:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

GACATTTCAT TAGGGCTTAT TAATTT 26

( 2 ) INFORMATION FOR SEQ ID NO:11:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

CAGCGGACGG CCAGACCGCA AG 22

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GTCGGAGTCA ACAACCTTAG GGGC 24

( 2 ) INFORMATION FOR SEQ ID NO:13:

( i ) SEQUENCE CHARACTERISTICS:
        ( A ) LENGTH: 21 base pairs (B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:13:

ATCCGGAAAA GCCGCTATGT C                              21

(2) INFORMATION FOR SEQ ID NO:14:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:14:

ATCCGGAAAA GCCGCTATGT C                              21

(2) INFORMATION FOR SEQ ID NO:15:

(i) SEQUENCE CHARACTERISTICS:
(A) LENGTH: 24 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:15:

GGCCAGAAAA TGGAAAAATT TGGG                           24

(2) INFORMATION FOR SEQ ID NO:16:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:16:

GTGGGTACAG GAGGTACCAA A                              21

(2) INFORMATION FOR SEQ ID NO:17:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:17:

GTGGGTACAG GAGGTACCAA A                              21

(2) INFORMATION FOR SEQ ID NO:18:

(i) SEQUENCE CHARACTERISTICS:
(A) LENGTH: 23 base pairs
(B) TYPE: nucleic acid
(C) STRANDEDNESS: single
(D) TOPOLOGY: linear (i i) MOLECULE TYPE: cDNA ( x i ) SEQUENCE DESCRIPTION: SEQ ID NO:18:

CGAAATACTA TGAGTGTAAC TGC 23

( 2 ) INFORMATION FOR SEQ ID NO:19:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

YTNGGNGGNY TNGCNGCNGT NAAYGCNGTN YTNCAYTTYT AYGARCCNMG NCCN 54

( 2 ) INFORMATION FOR SEQ ID NO:20:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

ATGATGTGAY YTTAYMGTAY YTGGGGYTGC GCGTAAYGCG TYTCAYTTYT AYGARCC 57

( 2 ) INFORMATION FOR SEQ ID NO:21:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

ATGAAACATC ATAAAAATTT TGATCATAT 29

( 2 ) INFORMATION FOR SEQ ID NO:22:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

TTGAATTCAT ATCTACTAAT GAGCAATCGA A 31

( 2 ) INFORMATION FOR SEQ ID NO:23:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

CCACACGCCT AGATTCTCAT GC 22

( 2 ) INFORMATION FOR SEQ ID NO:24:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

CGGGATCCAC AGTTACAGTC TGTAGCTCAA TTACCTACTT TTAACG     46

( 2 ) INFORMATION FOR SEQ ID NO:25:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

GGCCAAGGTT GCTGTAATAA TCG     23

( 2 ) INFORMATION FOR SEQ ID NO:26:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

CTCAATATTC TCGAAGCTGG GGCC     24

( 2 ) INFORMATION FOR SEQ ID NO:27:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

GCAGTCTGTA CGGAATTTAT ACA     23

( 2 ) INFORMATION FOR SEQ ID NO:28:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

CGAGGGTTAG CAGATAGCTA TG     22

( 2 ) INFORMATION FOR SEQ ID NO:29:

( i ) SEQUENCE CHARACTERISTICS:
        ( A ) LENGTH: 21 base pairs ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:29:

AAGATGGGGC GGTCTAACTC C                                                                                 21

( 2 ) INFORMATION FOR SEQ ID NO:30:

( i ) SEQUENCE CHARACTERISTICS:
                ( A ) LENGTH: 24 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:30:

GACCGTTATC GGGTGAATCT TTAG                                                                              24

( 2 ) INFORMATION FOR SEQ ID NO:31:

( i ) SEQUENCE CHARACTERISTICS:
                ( A ) LENGTH: 24 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:31:

TCGGCTGCAC TCTAAATTGT TGAG                                                                              24

( 2 ) INFORMATION FOR SEQ ID NO:32:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:32:

TATTGAGTGA ATTATGGGGG AT                                                                                22

( 2 ) INFORMATION FOR SEQ ID NO:33:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:33:

ATGTTCTAAA TTCTAACATA TCG                                                                               23

( 2 ) INFORMATION FOR SEQ ID NO:34:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:34:

TTATACCTAG ATCCTATTGT TG  22

( 2 ) INFORMATION FOR SEQ ID NO:35:

( i ) SEQUENCE CHARACTERISTICS:
　　　　( A ) LENGTH: 23 base pairs
　　　　( B ) TYPE: nucleic acid
　　　　( C ) STRANDEDNESS: single
　　　　( D ) TOPOLOGY: linear ( i i ) MOLECULE TYPE: cDNA ( x i ) SEQUENCE DESCRIPTION: SEQ ID NO:35:

TAACATTTCC ACACTTTTCA ATC  23

( 2 ) INFORMATION FOR SEQ ID NO:36:

( i ) SEQUENCE CHARACTERISTICS:
　　　　( A ) LENGTH: 19 base pairs
　　　　( B ) TYPE: nucleic acid
　　　　( C ) STRANDEDNESS: single
　　　　( D ) TOPOLOGY: linear ( i i ) MOLECULE TYPE: cDNA ( x i ) SEQUENCE DESCRIPTION: SEQ ID NO:36:

AAGGCTAGCG ACTGCTGTC  19

( 2 ) INFORMATION FOR SEQ ID NO:37:

( i ) SEQUENCE CHARACTERISTICS:
　　　　( A ) LENGTH: 287 amino acids
　　　　( B ) TYPE: amino acid
　　　　( C ) STRANDEDNESS: single
　　　　( D ) TOPOLOGY: linear ( i i ) MOLECULE TYPE: peptide ( x i ) SEQUENCE DESCRIPTION: SEQ ID NO:37:

| Met | Lys | His | His | Lys | Asn | Phe | Asp | His | Ile | Val | Trp | Asp | Phe | Ala | Glu |
| --- | --- | --- | --- | --- | --- | --- | --- | --- | --- | --- | --- | --- | --- | --- | --- |
| 1 | | | | 5 | | | | | 10 | | | | | 15 | |
| Lys | Trp | Thr | Glu | Gln | Lys | Gly | Val | Asp | Leu | Lys | Arg | Val | Ser | Tyr | Val |
| | | | 20 | | | | | 25 | | | | | 30 | | |
| Asp | Pro | Ile | Thr | Gly | Glu | Asp | Thr | Leu | Glu | Phe | Ile | Thr | Lys | Phe | Asn |
| | | | 35 | | | | 40 | | | | | 45 | | | |
| Tyr | Val | Gly | Lys | Leu | Glu | Glu | Lys | Ala | Tyr | Cys | Pro | Glu | Val | Ile | Glu |
| | | 50 | | | | | 55 | | | | | 60 | | | |
| Thr | Gln | Ser | Phe | Ser | Asn | Ser | Asn | Cys | Asp | Val | Ser | Arg | Glu | Phe | Leu |
| 65 | | | | | 70 | | | | | 75 | | | | | 80 |
| Lys | Lys | Lys | Val | Asp | Arg | Lys | Glu | Cys | Tyr | Leu | Trp | Asp | Ile | Asp | Tyr |
| | | | | 85 | | | | | 90 | | | | | 95 | |
| Gly | Phe | Ile | Ile | Pro | Thr | Ser | Val | Leu | Thr | Asn | Pro | Leu | Leu | Pro | Pro |
| | | | | 100 | | | | 105 | | | | | 110 | | |
| Thr | Leu | Asn | Glu | Lys | Ile | Asn | Pro | Ala | Met | Glu | Val | Asp | Leu | Phe | Lys |
| | | | 115 | | | | | 120 | | | | | 125 | | |
| Ser | Ala | Asn | Leu | Phe | Glu | Ser | Lys | Leu | Asn | Asn | Tyr | Arg | Met | Ile | Glu |
| | | 130 | | | | | 135 | | | | | 140 | | | |
| Ala | Gly | Val | Tyr | Ile | Glu | Pro | Asn | Gln | Ala | Val | Thr | Ala | Ser | Ile | Met |
| 145 | | | | | 150 | | | | | 155 | | | | | 160 |
| Val | Thr | Pro | Lys | Gln | Val | Gln | Gln | Asp | Tyr | Cys | Ile | Ser | Leu | Glu | Ile |
| | | | | 165 | | | | | 170 | | | | | 175 | |

| Ser | Gly | Ser | Ile | Ile | Ile | Glu | Leu | Lys | Asp | Ala | Tyr | Asn | Ala | Cys | Thr |
|---|---|---|---|---|---|---|---|---|---|---|---|---|---|---|---|
| | | | 180 | | | | 185 | | | | | | 190 | | |

| Asp | Lys | Glu | Thr | Ile | Glu | Thr | Ile | Phe | Tyr | Thr | Val | Pro | Ile | Ala | Asp |
|---|---|---|---|---|---|---|---|---|---|---|---|---|---|---|---|
| | | 195 | | | | 200 | | | | | | 205 | | | |

| Ile | Tyr | Arg | Ser | Glu | Leu | Ala | His | Asn | His | Ser | Phe | His | Leu | Asp | Gly |
|---|---|---|---|---|---|---|---|---|---|---|---|---|---|---|---|
| | 210 | | | | | 215 | | | | | 220 | | | | |

| Glu | Thr | Val | Ile | Phe | Thr | Gly | Lys | Gly | Thr | Phe | Lys | Gly | Leu | Ile | Cys |
|---|---|---|---|---|---|---|---|---|---|---|---|---|---|---|---|
| 225 | | | | | 230 | | | | | 235 | | | | | 240 |

| Ser | Asn | Ile | Phe | Val | Glu | Gly | Glu | Arg | Phe | Asp | Ser | Gln | Thr | Gly | Glu |
|---|---|---|---|---|---|---|---|---|---|---|---|---|---|---|---|
| | | | | 245 | | | | | 250 | | | | | 255 | |

| Cys | Leu | Gly | Lys | Tyr | Val | Ile | Pro | Leu | Ser | Ile | Glu | Lys | Lys | Asn | Asn |
|---|---|---|---|---|---|---|---|---|---|---|---|---|---|---|---|
| | | | 260 | | | | | 265 | | | | | 270 | | |

| Val | Asp | Cys | Ile | Ser | Ile | Phe | Leu | Asn | Ser | Glu | Lys | Gly | Gly | Ile | |
|---|---|---|---|---|---|---|---|---|---|---|---|---|---|---|---|
| | | 275 | | | | | 280 | | | | | 285 | | | |

(2) INFORMATION FOR SEQ ID NO:38:

(i) SEQUENCE CHARACTERISTICS:
        (A) LENGTH: 294 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

| Met | Ile | Val | Asp | Leu | Tyr | Arg | Tyr | Leu | Gly | Gly | Leu | Ala | Ala | Val | Asn |
|---|---|---|---|---|---|---|---|---|---|---|---|---|---|---|---|
| 1 | | | | 5 | | | | | 10 | | | | | 15 | |

| Ala | Val | Leu | His | Phe | Tyr | Glu | Pro | Arg | Pro | Asp | Ile | Cys | Arg | Asn | Ile |
|---|---|---|---|---|---|---|---|---|---|---|---|---|---|---|---|
| | | | 20 | | | | | 25 | | | | | 30 | | |

| Ser | Glu | Glu | Tyr | Asn | Leu | Ile | Val | Phe | Gly | Asp | Arg | Ile | Pro | Thr | Phe |
|---|---|---|---|---|---|---|---|---|---|---|---|---|---|---|---|
| | | 35 | | | | | 40 | | | | | 45 | | | |

| Ser | Ile | Asp | Pro | Ser | Gln | Ile | Asn | Ile | Asn | Asn | Leu | Ser | Val | Asp | Thr |
|---|---|---|---|---|---|---|---|---|---|---|---|---|---|---|---|
| | | 50 | | | | | 55 | | | | | 60 | | | |

| Pro | Val | Asp | Glu | Ile | Thr | Ile | Asn | Asn | Val | Arg | Ser | Ile | Gln | Leu | Ile |
|---|---|---|---|---|---|---|---|---|---|---|---|---|---|---|---|
| 65 | | | | | 70 | | | | | 75 | | | | | 80 |

| Ser | Ser | Arg | Phe | Glu | Asn | Thr | Gly | Phe | Val | Asp | Thr | Glu | Asn | Tyr | Phe |
|---|---|---|---|---|---|---|---|---|---|---|---|---|---|---|---|
| | | | | 85 | | | | | 90 | | | | | 95 | |

| Thr | Pro | Glu | Leu | Ser | Arg | Thr | Val | Val | Asn | Ser | Ile | Ser | Thr | Ser | Thr |
|---|---|---|---|---|---|---|---|---|---|---|---|---|---|---|---|
| | | | 100 | | | | | 105 | | | | | 110 | | |

| Thr | Thr | Gly | Tyr | Lys | Tyr | Thr | Gln | Ser | Leu | Thr | Val | Ser | Ser | Lys | Phe |
|---|---|---|---|---|---|---|---|---|---|---|---|---|---|---|---|
| | | 115 | | | | | 120 | | | | | 125 | | | |

| Ser | Phe | Asn | Phe | Pro | Val | Ala | Gly | Ala | Glu | Asn | Asn | Ile | Ser | Phe | Ser |
|---|---|---|---|---|---|---|---|---|---|---|---|---|---|---|---|
| | 130 | | | | | 135 | | | | | 140 | | | | |

| Val | Gly | Phe | Glu | Gln | Asn | Leu | Ser | Thr | Thr | Glu | Thr | Lys | Thr | Glu | Ser |
|---|---|---|---|---|---|---|---|---|---|---|---|---|---|---|---|
| 145 | | | | | 150 | | | | | 155 | | | | | 160 |

| Thr | Ser | Thr | Leu | Met | Arg | Ile | Pro | Pro | Gln | Pro | Val | Ser | Val | Arg | Pro |
|---|---|---|---|---|---|---|---|---|---|---|---|---|---|---|---|
| | | | | 165 | | | | | 170 | | | | | 175 | |

| Arg | Thr | Ala | Lys | Arg | Val | Glu | Ile | Ser | Leu | Phe | Glu | Leu | Ala | Ile | Pro |
|---|---|---|---|---|---|---|---|---|---|---|---|---|---|---|---|
| | | | 180 | | | | | 185 | | | | | 190 | | |

| Arg | Ile | Gln | Asn | Glu | Ile | Ser | Gly | Phe | Val | Thr | Gly | Thr | Leu | Pro | Thr |
|---|---|---|---|---|---|---|---|---|---|---|---|---|---|---|---|
| | | 195 | | | | | 200 | | | | | 205 | | | |

| Ile | Ser | Asn | Ser | His | Ile | Ser | Asp | Leu | Tyr | Ala | Val | Leu | Thr | Arg | Thr |
|---|---|---|---|---|---|---|---|---|---|---|---|---|---|---|---|
| | 210 | | | | | 215 | | | | | 220 | | | | |

| Asp | Ser | Leu | Cys | Pro | Asn | Ser | Tyr | Ile | Asn | Arg | Asp | Asp | Phe | Leu | Arg |
|---|---|---|---|---|---|---|---|---|---|---|---|---|---|---|---|
| 225 | | | | | 230 | | | | | 235 | | | | | 240 |

| Ile | Asp | His | Glu | Asn | Arg | Gly | Leu | Gly | Leu | Gln | Gly | Phe | Gly | Ser | Leu |
|---|---|---|---|---|---|---|---|---|---|---|---|---|---|---|---|
| | | | 245 | | | | 250 | | | | | | | 255 | |

| Thr | Gly | Asn | Leu | Thr | Ser | Leu | Asp | Phe | Ala | Ile | Arg | Thr | Glu | Tyr |
|---|---|---|---|---|---|---|---|---|---|---|---|---|---|---|
| | | | 260 | | | | | 265 | | | | 270 | | |

| Asp | Leu | Pro | Ser | Asn | Thr | Ile | Ile | Asn | Ile | Glu | Asn | Glu | Ile | Lys | Arg |
|---|---|---|---|---|---|---|---|---|---|---|---|---|---|---|---|
| | | 275 | | | | | 280 | | | | | 285 | | | |

| Ala | His | Ile | Leu | Thr | Gln |
|---|---|---|---|---|---|
| 290 | | | | | |

(2) INFORMATION FOR SEQ ID NO:39:

(i) SEQUENCE CHARACTERISTICS:
        (A) LENGTH: 864 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

| | | | | | |
|---|---|---|---|---|---|
| ATGAAACATC | ATAAAAATTT | TGATCACATA | GTTTGGGACT | TCGCTGAAAA | GTGGACTGAA | 60 |
| CAAAGGGGG | TAGATTTAAA | AAGGGTCAGT | TATGTAGATC | CCATTACTGG | TGAAGATACA | 120 |
| TTAGAGTTTA | TAACCAAATT | TAATTATGTT | GGGAAATTAG | AAGAAAAAGC | TTATTGTCCA | 180 |
| GAAGTAATAG | AAACACAATC | TTTTTCAAAC | TCAAATTGTG | ACGTTTCGAG | GAATTTCTA | 240 |
| AAGAAAAAG | TAGACAGGAA | GGAATGTTAT | TTATGGGATA | TAGACTATGG | GTTTATTATA | 300 |
| CCAACTTCGG | TACTTACAAA | TCCATTATTA | CCCCCCACTC | TCAATGAAAA | AATTAATCCA | 360 |
| GCAATGGAAG | TGGACTTATT | TAAAAGTGCA | AACCTGTTTG | AATCCAAACT | AAATAATTAT | 420 |
| AGAATGATAG | AAGCAGGTGT | TTATATTGAA | CCAAATCAAG | CAGTAACCGC | CAGCATAATG | 480 |
| GTTACACCAA | AACAAGTACA | GCAAGATTAT | TGTATTAGCC | TTGAGATTTC | AGGTAGTATT | 540 |
| ATCATTGAGC | TGAAAGATGC | TTATAATGCT | TGTACAGATA | AAGAAACTAT | TGAAACAATA | 600 |
| TTCTATACCG | TGCCAATTGC | AGATATATAC | AGATCCGAGC | TTGCCCATAA | CCATTCCTTT | 660 |
| CATTTAGATG | GAGAAACTGT | AATATTTACA | GGGAAAGGTA | CGTTAAAGG | CTTAATATGT | 720 |
| TCTAATATAT | TTGTTGAAGG | GGAAAGATTC | GATTCTCAAA | CGGGGGAATG | TTTGGGGAAA | 780 |
| TATGTGATCC | CATTAAGTAT | AGAAAAGAAA | AATAATGTAG | ATTGTATCTC | TATATTTTA | 840 |
| AATTCAGAAA | AAGGTGGGAT | TTAA | | | | 864 |

(2) INFORMATION FOR SEQ ID NO:40:

(i) SEQUENCE CHARACTERISTICS:
        (A) LENGTH: 885 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

| | | | | | |
|---|---|---|---|---|---|
| ATGATAGTAG | ATTTATATAG | ATATTTAGGT | GGATTGGCAG | CAGTAAATGC | CGTACTTCAC | 60 |
| TTTTATGAGC | CACGCCCTGA | TATATGTAGG | AATATAAGCG | AAGAATATAA | CCTTATAGTA | 120 |
| TTTGGAGACC | GTATACCAAC | TTTTAGCATA | GATCCTTCGC | AAATAAATAT | TAACAATTTA | 180 |
| TCTGTGGACA | CTCCAGTGGA | TGAAATAACT | ATTAATAACG | TGAGAAGTAT | ACAATTAATA | 240 |
| TCTAGTCGTT | TTGAAAATAC | AGGATTTGTC | GATACTGAAA | ATTATTTTAC | TCCTGAATTA | 300 |
| TCTAGAACAG | TTGTAAATAG | CATATCTACA | TCGACTACTA | CAGGATATAA | GTACACTCAA | 360 |

| | | | | | |
|---|---|---|---|---|---|
| TCCCTTACTG | TTTCATCCAA | ATTCTCCTTT | AATTTCCCAG | TTGCGGGTGC | AGAAAATAAT | 420 |
| ATTTCATTTT | CAGTAGGTTT | TGAACAAAAC | CTTTCAACTA | CAGAAACTAA | AACAGAAAGT | 480 |
| ACTTCAACGC | TTATGCGTAT | ACCTCCACAA | CCAGTTTCCG | TAAGACCCAG | AACAGCAAAA | 540 |
| AGGGTTGAAA | TATCGCTCTT | TGAATTGGCA | ATCCCTAGAA | TACAAAACGA | AATTTCCGGA | 600 |
| TTTGTAACAG | GTACTCTTCC | AACAATTTCA | AATTCGCATA | TTTCCGATCT | TTATGCTGTA | 660 |
| TTAACACGGA | CTGATAGCCT | ATGCCCTAAT | TCATATATTA | ACCGAGATGA | CTTTTAAGA | 720 |
| ATAGATCATG | AAAATAGGGG | TTTGGGATTA | CAAGGCTTCG | GTTCTCTCAC | TGGAAATTTA | 780 |
| ACATCATTAG | ATTTTGCAAT | TAGAACTACT | GAATATGATT | TACCTTCAAA | TACAATTATA | 840 |
| AATATAGAGA | ACGAAATAAA | AAGAGCCCAT | ATACTCACAC | AGTAA | | 885 |

(2) INFORMATION FOR SEQ ID NO:41:

(i) SEQUENCE CHARACTERISTICS:
        (A) LENGTH: 2101 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

| | | | | | |
|---|---|---|---|---|---|
| ATTAAACACT | AAATACATTC | ACATTATTCT | AACAAAGAAA | AGGAGTAATA | ATTATGAAAC | 60 |
| ATCATAAAAA | TTTTGATCAC | ATAGTTTGGG | ACTTCGCTGA | AAAGTGGACT | GAACAAAAGG | 120 |
| GGGTAGATTT | AAAAAGGGTC | AGTTATGTAG | ATCCCATTAC | TGGTGAAGAT | ACATTAGAGT | 180 |
| TTATAACCAA | ATTTAATTAT | GTTGGGAAAT | TAGAAGAAAA | AGCTTATTGT | CCAGAAGTAA | 240 |
| TAGAAACACA | ATCTTTTTCA | AACTCAAATT | GTGACGTTTC | GAGGGAATTT | CTAAAGAAAA | 300 |
| AAGTAGACAG | GAAGGAATGT | TATTTATGGG | ATATAGACTA | TGGGTTTATT | ATACCAACTT | 360 |
| CGGTACTTAC | AAATCCATTA | TTACCCCCCA | CTCTCAATGA | AAAAATTAAT | CCAGCAATGG | 420 |
| AAGTGGACTT | ATTTAAAAGT | GCAAACCTGT | TTGAATCCAA | ACTAAATAAT | TATAGAATGA | 480 |
| TAGAAGCAGG | TGTTTATATT | GAACCAAATC | AAGCAGTAAC | CGCCAGCATA | ATGGTTACAC | 540 |
| CAAAACAAGT | ACAGCAAGAT | TATTGTATTA | GCCTTGAGAT | TTCAGGTAGT | ATTATCATTG | 600 |
| AGCTGAAAGA | TGCTTATAAT | GCTTGTACAG | ATAAAGAAAC | TATTGAAACA | ATATTCTATA | 660 |
| CCGTGCCAAT | TGCAGATATA | TACAGATCCG | AGCTTGCCCA | TAACCATTCC | TTTCATTTAG | 720 |
| ATGGAGAAAC | TGTAATATTT | ACAGGGAAAG | GTACGTTTAA | AGGCTTAATA | TGTTCTAATA | 780 |
| TATTTGTTGA | AGGGGAAAGA | TTCGATTCTC | AAACGGGGGA | ATGTTTGGGG | AAATATGTGA | 840 |
| TCCCATTAAG | TATAGAAAAG | AAAAATAATG | TAGATTGTAT | CTCTATATTT | TTAAATTCAG | 900 |
| AAAAAGGTGG | GATTTAACAT | GATAGTAGAT | TTATATAGAT | ATTTAGGTGG | ATTGGCAGCA | 960 |
| GTAAATGCCG | TACTTCACTT | GATTTAAACA | TGATAGTAGA | TTTATATAGA | TATTTAGGTG | 1020 |
| GATTGGCAGC | AGTAAATGCC | GTACTTCACT | TTTATGAGCC | ACGCCCTGAT | ATATGTAGGA | 1080 |
| ATATAAGCGA | AGAATATAAC | CTTATAGTAT | TGGAGACCG | TATACCAACT | TTTAGCATAG | 1140 |
| ATCCTTCGCA | AATAAATATT | AACAATTTAT | CTGTGGACAC | TCCAGTGGAT | GAAATAACTA | 1200 |
| TTAATAACGT | GAGAAGTATA | CAATTAATAT | CTAGTCGTTT | TGAAAATACA | GGATTTGTCG | 1260 |
| ATACTGAAAA | TTATTTTACT | CCTGAATTAT | CTAGAACAGT | TGTAAATAGC | ATATCTACAT | 1320 |
| CGACTACTAC | AGGATATAAG | TACACTCAAT | CCCTTACTGT | TTCATCCAAA | TTCTCCTTTA | 1380 |
| ATTTCCCAGT | TGCGGGTGCA | GAAAATAATA | TTTCATTTTC | AGTAGGTTTT | GAACAAAACC | 1440 |
| TTTCAACTAC | AGAAACTAAA | ACAGAAAGTA | CTTCAACGCT | TATGCGTATA | CCTCCACAAC | 1500 |

```
CAGTTTCCGT  AAGACCCAGA  ACAGCAAAAA  GGGTTGAAAT  ATCGCTCTTT  GAATTGGCAA     1560

TCCCTAGAAT  ACAAAACGAA  ATTTCCGGAT  TTGTAACAGG  TACTCTTCCA  ACAATTTCAA     1620

ATTCGCATAT  TTCCGATCTT  TATGCTGTAT  TAACACGGAC  TGATAGCCTA  TGCCCTAATT     1680

CATATATTAA  CCGAGATGAC  TTTTTAAGAA  TAGATCATGA  AAATAGGGGT  TTGGGATTAC     1740

AAGGCTTCGG  TTCTCTCACT  GGAAATTTAA  CATCATTAGA  TTTTGCAATT  AGAACTACTG     1800

AATATGATTT  ACCTTCAAAT  ACAATTATAA  ATATAGAGAA  CGAAATAAAA  AGAGCCCATA     1860

TACTCACACA  GTAATTAATA  GAAATAGACC  GATAATCGGT  CTTCCCCTG   TCAAGTAGGC     1920

CTAGTGACAG  GGTTCTTGCT  GTGGACCGCA  AGGTAGCAAA  TTTCTGAAGA  CCCATATGGG     1980

GTACCGTCAG  GAAAATGCGG  ATTTACAACG  CTAAGCCCAT  TTTCCTGACG  ATTCCCCCAT     2040

TTTTAACAAC  GTTAAGAAAG  TTTCAATGGT  CTTAAAGAAT  CTAATGAGAT  CATTTCTCC     2100

G                                                                         2101
```

( 2 ) INFORMATION FOR SEQ ID NO:42:

( i ) SEQUENCE CHARACTERISTICS:
( A ) LENGTH: 310 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:42:

```
Met  Ala  Ile  Met  Asn  Pro  Arg  Pro  Asp  Ile  Ala  Gln  Asp  Ala  Ala  Arg
 1              5                        10                       15

Ala  Trp  Asp  Ile  Ile  Ala  Gly  Pro  Phe  Ile  Arg  Pro  Gly  Thr  Thr  Pro
               20                       25                       30

Thr  Asn  Arg  Gln  Leu  Phe  Asn  Tyr  Gln  Ile  Gly  Asn  Ile  Glu  Val  Glu
              35                        40                       45

Thr  Pro  Pro  Gly  Asn  Leu  Asn  Phe  Ser  Val  Val  Pro  Glu  Leu  Asp  Phe
     50                        55                       60

Ser  Val  Ser  Gln  Asp  Leu  Phe  Asn  Asn  Thr  Ser  Val  Gln  Gln  Ser  Gln
65                        70                       75                       80

Thr  Tyr  Ala  Ser  Phe  Asn  Glu  Ser  Arg  Thr  Val  Val  Glu  Thr  Thr  Ser
                    85                       90                       95

Thr  Ala  Val  Thr  His  Gly  Val  Lys  Ser  Gly  Val  Thr  Val  Ser  Ala  Ser
                    100                      105                      110

Ala  Lys  Phe  Asn  Ala  Lys  Ile  Leu  Val  Lys  Ser  Ile  Glu  Gln  Thr  Ile
               115                      120                      125

Thr  Thr  Thr  Val  Ser  Thr  Glu  Tyr  Asn  Phe  Ser  Ser  Thr  Thr  Thr  Arg
     130                      135                      140

Thr  Asn  Thr  Val  Thr  Arg  Gly  Trp  Ser  Ile  Pro  Ala  Gln  Pro  Val  Leu
145                      150                      155                      160

Val  Pro  Pro  His  Ser  Arg  Val  Thr  Ala  Thr  Leu  Gln  Ile  Tyr  Lys  Gly
                    165                      170                      175

Asp  Phe  Thr  Val  Pro  Val  Leu  Gln  Asn  Glu  Leu  Ser  Leu  Arg  Val  Tyr
               180                      185                      190

Gly  Gln  Thr  Gly  Thr  Leu  Pro  Ala  Gly  Asn  Pro  Ser  Phe  Pro  Ser  Asp
          195                      200                      205

Leu  Tyr  Ala  Val  Ala  Thr  Tyr  Glu  Asn  Thr  Leu  Leu  Gly  Arg  Ile  Arg
     210                      215                      220

Glu  His  Ile  Ala  Pro  Pro  Ala  Leu  Phe  Arg  Ala  Ser  Asn  Ala  Tyr  Ile
225                      230                      235                      240
```

```
Ser  Asn  Gly  Val  Gln  Ala  Ile  Trp  Arg  Gly  Thr  Ala  Thr  Thr  Arg  Val
               245                      250                      255

Ser  Gln  Gly  Leu  Tyr  Ser  Val  Val  Arg  Ile  Asp  Glu  Arg  Pro  Leu  Ala
               260                      265                      270

Gly  Tyr  Ser  Gly  Glu  Thr  Arg  Thr  Glu  Tyr  Tyr  Leu  Pro  Val  Thr  Leu
               275                      280                      285

Ser  Asn  Ser  Ser  Gln  Ile  Leu  Thr  Pro  Gly  Ser  Leu  Gly  Ser  Glu  Ile
               290                      295                      300

Pro  Ile  Ile  Asn  Pro  Val
305                 310
```

( 2 ) INFORMATION FOR SEQ ID NO:43:

( i ) SEQUENCE CHARACTERISTICS:
( A ) LENGTH: 358 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:43:

```
Trp  Val  Arg  Tyr  Asn  Gln  Phe  Arg  Arg  Glu  Leu  Thr  Leu  Thr  Val  Leu
1                   5                        10                       15

Asp  Ile  Val  Ala  Leu  Phe  Ser  Asn  Tyr  Asp  Ser  Arg  Arg  Tyr  Pro  Gly
               20                       25                       30

Gly  Ile  Arg  Thr  Val  Ser  Gln  Leu  Thr  Arg  Glu  Ile  Tyr  Thr  Asn  Pro
               35                       40                       45

Val  Leu  Cys  Glu  Asn  Phe  Ser  Glu  Asp  Gly  Ser  Phe  Arg  Gly  Met  Ala
     50                       55                       60

Gln  Arg  Ile  Glu  Gln  Asn  Ile  Arg  Gln  Pro  His  Leu  Met  Asp  Ile  Leu
65                       70                       75                       80

Asn  Ser  Ile  Thr  Ile  Tyr  Thr  Asp  Val  His  Arg  Gly  Phe  Asn  Tyr  Trp
               85                       90                       95

Ser  Gly  His  Gln  Ile  Thr  Ala  Ser  Pro  Val  Gly  Phe  Ser  Gly  Pro  Glu
               100                      105                      110

Phe  Ala  Phe  Pro  Leu  Phe  Gly  Asn  Ala  Gly  Asn  Ala  Ala  Pro  Pro  Val
               115                      120                      125

Leu  Val  Ser  Leu  Thr  Gly  Leu  Gly  Ile  Phe  Arg  Thr  Leu  Ser  Ser  Pro
     130                      135                      140

Leu  Tyr  Arg  Tyr  Thr  Gln  Arg  Ile  Ile  Leu  Gly  Ser  Gly  Pro  Asn  Asn
145                      150                      155                      160

Gln  Glu  Leu  Phe  Val  Leu  Asp  Gly  Thr  Glu  Asn  Asn  Phe  Ser  Phe  Ala
               165                      170                      175

Ser  Leu  Thr  Thr  Asn  Leu  Pro  Ser  Thr  Ile  Tyr  Arg  Gln  Arg  Gly  Thr
               180                      185                      190

Val  Asp  Ser  Leu  Asp  Val  Ile  Pro  Pro  Gln  Asp  Asn  Ser  Val  Pro  Pro
               195                      200                      205

Arg  Ala  Gly  Lys  Arg  Val  Glu  Phe  Ser  Leu  His  Arg  Leu  Ser  His  Val
     210                      215                      220

Thr  Met  Leu  Ser  Gln  Ala  Ala  Gly  Ala  Val  Tyr  Thr  Leu  Arg  Ala  Pro
225                      230                      235                      240

Thr  Phe  Ser  Trp  Gln  His  Arg  Ser  Ala  Glu  Phe  Asn  Asn  Ile  Ile  Pro
               245                      250                      255

Ser  Ser  Gln  Ser  Leu  Ile  Thr  Gln  Ile  Pro  Leu  Thr  Lys  Ser  Thr  Asn
               260                      265                      270
```

|  |  | Leu | Gly | Ser<br>275 | Gly | Thr | Ser | Val | Val<br>280 | Lys | Gly | Pro | Gly<br>285 | Phe | Thr | Gly | Gly |
|---|---|---|---|---|---|---|---|---|---|---|---|---|---|---|---|---|---|
|  |  | Asp | Ile<br>290 | Leu | Arg | Arg | Thr | Ser<br>295 | Pro | Gly | Gln | Ile | Ser<br>300 | Thr | Leu | Arg | Val |
|  |  | Asn<br>305 | Ile | Thr | Ala | Pro | Leu<br>310 | Ser | Gln | Arg | Tyr | Arg<br>315 | Val | Arg | Ile | Arg | Tyr<br>320 |
|  |  | Ala | Ser | Thr | Thr | Asn<br>325 | Leu | Gln | Phe | His | Thr<br>330 | Ser | Ile | Asp | Gly | Arg<br>335 | Pro |
|  |  | Ile | Asn | Gln | Gly<br>340 | Asn | Phe | Ser | Ala | Thr<br>345 | Met | Ser | Ser | Gly | Ser<br>350 | Asn | Leu |
|  |  | Gln | Ser | Gly<br>355 | Ser | Phe | Arg |  |  |  |  |  |  |  |  |  |  |

( 2 ) INFORMATION FOR SEQ ID NO:44:

( i ) SEQUENCE CHARACTERISTICS:
        ( A ) LENGTH: 980 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

| ATTAAACACT | AAATACATTC | ACATTATTCT | AACAAAGAAA | AGGAGTAATA | ATTATGAAAC | 60 |
|---|---|---|---|---|---|---|
| ATCATAAAAA | TTTTGATCAC | ATAGTTTGGG | ACTTCGCTGA | AAAGTGGACT | GAACAAAAGG | 120 |
| GGGTAGATTT | AAAAAGGGTC | AGTTATGTAG | ATCCCATTAC | TGGTGAAGAT | ACATTAGAGT | 180 |
| TTATAACCAA | ATTTAATTAT | GTTGGGAAAT | TAGAAGAAAA | AGCTTATTGT | CCAGAAGTAA | 240 |
| TAGAAACACA | ATCTTTTTCA | AACTCAAATT | GTGACGTTTC | GAGGGAATTT | CTAAAGAAAA | 300 |
| AAGTAGACAG | GAAGGAATGT | TATTTATGGG | ATATAGACTA | TGGGTTTATT | ATACCAACTT | 360 |
| CGGTACTTAC | AAATCCATTA | TTACCCCCCA | CTCTCAATGA | AAAAATTAAT | CCAGCAATGG | 420 |
| AAGTGGACTT | ATTTAAAAGT | GCAAACCTGT | TTGAATCCAA | ACTAAATAAT | TATAGAATGA | 480 |
| TAGAAGCAGG | TGTTTATATT | GAACCAAATC | AAGCAGTAAC | CGCCAGCATA | ATGGTTACAC | 540 |
| CAAAACAAGT | ACAGCAAGAT | TATTGTATTA | GCCTTGAGAT | TTCAGGTAGT | ATTATCATTG | 600 |
| AGCTGAAAGA | TGCTTATAAT | GCTTGTACAG | ATAAAGAAAC | TATTGAAACA | ATATTCTATA | 660 |
| CCGTGCCAAT | TGCAGATATA | TACAGATCCG | AGCTTGCCCA | TAACCATTCC | TTTCATTTAG | 720 |
| ATGGAGAAAC | TGTAATATTT | ACAGGGAAAG | GTACGTTTAA | AGGCTTAATA | TGTTCTAATA | 780 |
| TATTTGTTGA | AGGGGAAAGA | TTCGATTCTC | AAACGGGGGA | ATGTTTGGGG | AAATATGTGA | 840 |
| TCCCATTAAG | TATAGAAAAG | AAAAATAATG | TAGATTGTAT | CTCTATATTT | TTAAATTCAG | 900 |
| AAAAAGGTGG | GATTTAACAT | GATAGTAGAT | TTATATAGAT | ATTTAGGTGG | ATTGGCAGCA | 960 |
| GTAAATGCCG | TACTTCACTT |  |  |  |  | 980 |

( 2 ) INFORMATION FOR SEQ ID NO:45:

( i ) SEQUENCE CHARACTERISTICS:
        ( A ) LENGTH: 1121 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

| GATTTAAACA | TGATAGTAGA | TTTATATAGA | TATTTAGGTG | GATTGGCAGC | AGTAAATGCC | 60 |
|---|---|---|---|---|---|---|

-continued

| | | | | | | |
|---|---|---|---|---|---|---|
| GTACTTCACT | TTTATGAGCC | ACGCCCTGAT | ATATGTAGGA | ATATAAGCGA | AGAATATAAC | 120 |
| CTTATAGTAT | TTGGAGACCG | TATACCAACT | TTTAGCATAG | ATCCTTCGCA | AATAAATATT | 180 |
| AACAATTTAT | CTGTGGACAC | TCCAGTGGAT | GAAATAACTA | TTAATAACGT | GAGAAGTATA | 240 |
| CAATTAATAT | CTAGTCGTTT | TGAAAATACA | GGATTTGTCG | ATACTGAAAA | TTATTTTACT | 300 |
| CCTGAATTAT | CTAGAACAGT | TGTAAATAGC | ATATCTACAT | CGACTACTAC | AGGATATAAG | 360 |
| TACACTCAAT | CCCTTACTGT | TTCATCCAAA | TTCTCCTTTA | ATTTCCAGT | TGCGGGTGCA | 420 |
| GAAATAATA | TTTCATTTTC | AGTAGGTTTT | GAACAAAACC | TTTCAACTAC | AGAAACTAAA | 480 |
| ACAGAAAGTA | CTTCAACGCT | TATGCGTATA | CCTCCACAAC | CAGTTTCCGT | AAGACCCAGA | 540 |
| ACAGCAAAAA | GGGTTGAAAT | ATCGCTCTTT | GAATTGGCAA | TCCCTAGAAT | ACAAAACGAA | 600 |
| ATTTCCGGAT | TTGTAACAGG | TACTCTTCCA | ACAATTTCAA | ATTCGCATAT | TTCCGATCTT | 660 |
| TATGCTGTAT | TAACACGGAC | TGATAGCCTA | TGCCCTAATT | CATATATTAA | CCGAGATGAC | 720 |
| TTTTTAAGAA | TAGATCATGA | AAATAGGGGT | TTGGGATTAC | AAGGCTTCGG | TTCTCTCACT | 780 |
| GGAAATTTAA | CATCATTAGA | TTTTGCAATT | AGAACTACTG | AATATGATTT | ACCTTCAAAT | 840 |
| ACAATTATAA | ATATAGAGAA | CGAAATAAAA | AGAGCCCATA | TACTCACACA | GTAATTAATA | 900 |
| GAAATAGACC | GATAATCGGT | CTTCCCCCTG | TCAAGTAGGC | CTAGTGACAG | GGTTCTTGCT | 960 |
| GTGGACCGCA | AGGTAGCAAA | TTTCTGAAGA | CCCATATGGG | GTACCGTCAG | GAAAATGCGG | 1020 |
| ATTTACAACG | CTAAGCCCAT | TTTCCTGACG | ATTCCCCCAT | TTTTAACAAC | GTTAAGAAAG | 1080 |
| TTTCAATGGT | CTTAAAGAAT | CTAATGAGAT | CATTTCTCC | G | | 1121 |

What is claimed is:

1. A nucleic acid fragment containing a nucleic acid sequence as depicted in Seq. I.D. No.37 and encoding a delta-endotoxin or a portion of said delta-endotoxin having insecticidal activity against an insect pest of the order of Lepidoptera.

2. A nucleic acid fragment containing a nucleic acid sequence as depicted in Seq. I.D. No.38 and encoding a delta-endotoxin or a portion of said delta-endotoxin having insecticidal activity against an insect pest of the order of Lepidoptera.

3. A nucleic acid fragment containing a nucleic acid sequence as depicted in SEQ ID NO:39.

4. A nucleic acid fragment containing a nucleic acid sequence as depicted in SEQ ID NO:40.

5. A nucleic acid fragment containing a nucleic acid sequence as depicted in SEQ ID NO:41.

6. A nucleic acid fragment containing a nucleic acid sequence as depicted in SEQ ID NO:44.

7. A nucleic acid fragment containing a nucleic acid sequence as depicted in SEQ ID NO:45.

8. A DNA construct comprising the nucleic acid fragment of claim 1.

9. A DNA construct comprising the nucleic acid fragment of claim 2.

10. A DNA construct comprising the nucleic acid fragment of claim 3.

11. A DNA construct comprising the nucleic acid fragment of claim 4.

12. A DNA construct comprising the nucleic acid fragment of claim 5.

13. A DNA construct comprising the nucleic acid fragment of claim 6.

14. A DNA construct comprising the nucleic acid fragment of claim 7.

15. A recombinant DNA vector comprising (a) the DNA construct of claim 8; (b) a promoter operably linked to the DNA sequence of (a); and (c) a selectable marker.

16. A recombinant DNA vector comprising (a) the DNA construct of claim 9; (b) a promoter operably linked to the DNA sequence of (a); and (c) a selectable marker.

17. A recombinant DNA vector comprising (a) the DNA construct of claim 10; (b) a promoter operably linked to the DNA sequence of (a); and (c) a selectable marker.

18. A recombinant DNA vector comprising (a) the DNA construct of claim 11; (b) a promoter operably linked to the DNA sequence of (a); and (c) a selectable marker.

19. A recombinant DNA vector comprising (a) the DNA construct of claim 12; (b) a promoter operably linked to the DNA sequence of (a); and (c) a selectable marker.

20. A recombinant DNA vector comprising (a) the DNA construct of claim 13; (b) a promoter operably linked to the DNA sequence of (a); and (c) a selectable marker.

21. A recombinant DNA vector comprising (a) the DNA construct of claim 14; (b) a promoter operably linked to the DNA sequence of (a); and (c) a selectable marker.

22. A host cell comprising a heterologous nucleic acid containing a nucleic acid sequence as depicted in Seq. I.D. No.37 encoding a delta-endotoxin or a portion of said delta-endotoxin having insecticidal activity against an insect pest of the order of Lepidoptera.

23. A host cell comprising a heterologous nucleic acid containing a nucleic acid sequence as depicted in Seq. I.D. No.38 encoding a delta-endotoxin or a portion of said delta-endotoxin having insecticidal activity against an insect pest of the order of Lepidoptera.

24. A host cell comprising the DNA construct of claim 3.
25. A host cell comprising the DNA construct of claim 4.
26. A host cell comprising the DNA construct of claim 5.
27. A host cell comprising the DNA construct of claim 6.
28. A host cell comprising the DNA construct of claim 7.

* * * * *